United States Patent
Tsunoda et al.

(10) Patent No.: US 10,542,895 B2
(45) Date of Patent: Jan. 28, 2020

(54) BLOOD PRESSURE MEASUREMENT CUFF AND BLOOD PRESSURE MONITOR INCLUDING THE SAME

(71) Applicant: OMRON HEALTHCARE CO., LTD., Muko-shi, Kyoto (JP)

(72) Inventors: Wataru Tsunoda, Kyoto (JP); Naomi Matsumura, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 467 days.

(21) Appl. No.: 15/175,387

(22) Filed: Jun. 7, 2016

(65) Prior Publication Data

US 2016/0287104 A1   Oct. 6, 2016

Related U.S. Application Data

(63) Continuation of application No. PCT/JP2014/082934, filed on Dec. 12, 2014.

(30) Foreign Application Priority Data

Dec. 27, 2013  (JP) ................................. 2013-272338

(51) Int. Cl.
*A61B 5/022* (2006.01)
*A61B 5/00* (2006.01)
(Continued)

(52) U.S. Cl.
CPC ........ *A61B 5/02233* (2013.01); *A61B 5/6824* (2013.01); *A61B 5/022* (2013.01);
(Continued)

(58) Field of Classification Search
CPC . A61B 5/02233; A61B 5/02141; A61B 5/022; A61B 5/02208; A61B 5/6824; Y10S 128/15
See application file for complete search history.

(56) References Cited

U.S. PATENT DOCUMENTS 3,752,147 A * 8/1973 Castro ................ A61B 5/02233
                                                    128/DIG. 20
5,615,088 A * 3/1997 Mizumo .............. H05K 1/0281
                                                    174/260
(Continued)

FOREIGN PATENT DOCUMENTS

CN         1320411 A    11/2000
JP       H09-38053 A     2/1997
(Continued)

OTHER PUBLICATIONS

Feb. 17, 2015 International Search Report issued in International Patent Application No. PCT/JP2014/082934.
(Continued)

*Primary Examiner* — Christian Jang
*Assistant Examiner* — Karen E Toth
(74) *Attorney, Agent, or Firm* — Oliff PLC

(57) ABSTRACT

A blood pressure measurement cuff is worn on a measurement site that extends in longitudinal direction in substantial round bar shape and gradually becomes thinner from one side to another side in longitudinal direction. A band-shaped body is included which is configured to contain an air bladder between an inner cloth that is to come into contact with the measurement site and an outer cloth that opposes the inner cloth, the band-shaped body being configured to be wrapped in a circumferential direction around the measurement site. A plate member is included which is provided between the outer cloth and the air bladder in a thickness direction and in a region that corresponds to at least a portion in the circumferential direction of the band-shaped body. The thickness of the plate member gradually becomes thinner from the one side to the other side in the longitudinal direction.

10 Claims, 13 Drawing Sheets

(51) Int. Cl.
*A61B 5/0235* (2006.01)
*A61B 5/021* (2006.01)

(52) U.S. Cl.
CPC ......... *A61B 5/0235* (2013.01); *A61B 5/02141* (2013.01); *A61B 5/02208* (2013.01)

(56) References Cited

U.S. PATENT DOCUMENTS

| | | | | |
|---|---|---|---|---|
| 5,660,182 A | * | 8/1997 | Kuroshaki | ......... A61B 5/02233 600/499 |
| 2004/0186385 A1 | * | 9/2004 | Mochizuki | ......... A61B 5/02141 600/499 |
| 2010/0137725 A1 | * | 6/2010 | Takahashi | .......... A61B 5/02233 600/493 |
| 2010/0317945 A1 | * | 12/2010 | Schraa | ............... A61B 5/02241 600/324 |

FOREIGN PATENT DOCUMENTS

| | | |
|---|---|---|
| JP | 2002-209858 A | 7/2002 |
| JP | 2005-237424 A | 9/2005 |
| JP | 2006-149682 A | 6/2006 |
| JP | 2008-237520 A | 10/2008 |

OTHER PUBLICATIONS

Feb. 23, 2018 Office Action issued in Chinese Patent Application No. 201480066633.0.

* cited by examiner

BLOOD PRESSURE MEASUREMENT CUFF AND BLOOD PRESSURE MONITOR INCLUDING THE SAME

TECHNICAL FIELD

The present invention relates to a blood pressure measurement cuff, and more specifically relates to a cuff that is wrapped around and compresses a measurement site such as an arm or a wrist of a measurement subject in order to perform blood pressure measurement.

The present invention also relates to a blood pressure monitor including such a blood pressure measurement cuff.

BACKGROUND ART

Conventionally, as this type of blood pressure monitor as disclosed in Patent Literature 1 (JP 2006-149682A) for example, a wrist-type blood pressure monitor is known which includes a cuff that is equipped with an air bladder and is to be wrapped around a wrist serving as a measurement site, and a blood pressure measurement main body that is integrally bonded with the cuff.

CITATION LIST

Patent Literature

Patent Literature 1: JP 2006-149682A

SUMMARY OF INVENTION

Technical Problem

Incidentally, as shown schematically in FIG. 23, a wrist 90 serving as a measurement site has an approximate round bar shape and gradually becomes thinner from an elbow side 90e to a hand side 90f. For this reason, with a conventional wrist-type blood pressure monitor (in this example, a rectangular frame 110 schematically indicates a blood pressure monitor main body), when air is supplied to a cuff 120 (or more accurately, to an air bladder) while the cuff 120 is wrapped around the wrist in order to perform blood pressure measurement, an outer cloth 120A of the cuff 120 receives outward forces f1, f1, . . . that are inclined toward the hand side 90f with respect to a longitudinal direction 90c of the wrist. Reference numeral F1 indicates a combined force obtained by combining the outward forces f1, f1, . . . . A component Fir of the outward force F1, which is perpendicular to the longitudinal direction 90c of the wrist, is canceled out upon being combined around the wrist, and a component Fly of the outward force F1, which is parallel to the longitudinal direction 90c of the wrist, remains. On the other hand, an inner cloth 120B of the cuff 120 receives an inward force (combined force) F2 that is inclined toward the elbow side 90e with respect to the longitudinal direction 90c of the wrist. A component F2r of the inward force F2, which is perpendicular to the longitudinal direction 90c of the wrist, is canceled out upon being combined around the wrist, and a component F2y of the outward force F2, which is parallel to the longitudinal direction 90c of the wrist, remains. As shown schematically in FIG. 24, the inner cloth 120B of the cuff 120 receives a friction force F2y# from the measurement site 90 in a direction of canceling out the component F2y. As a result, the cuff 120 moves toward the hand side 90f (position shifting in the direction indicated by arrow C) in a situation in which the outer cloth 120A and the inner cloth 120B rotate. Also, accompanying this position shifting, the volume of the air bladder expands and compression loss occurs, as indicated by a two-point chain line 120' in FIG. 24. As a result, there is a problem in that an artery at the measurement site cannot be compressed suitably.

In view of this, the present invention aims to provide a blood pressure measurement cuff that can prevent the occurrence of position shifting with respect to the measurement site (hereinafter referred to as "position shifting") and compression loss.

Also, the present invention aims to provide a blood pressure monitor including such a cuff.

Solution to Problem

In order to solve the foregoing problems, a blood pressure measurement cuff according to the present invention is a blood pressure measurement cuff to be worn on a measurement site that extends in a longitudinal direction substantially in a round bar shape and gradually becomes thinner from one side to another side in the longitudinal direction, including:

a band-shaped body configured to contain an air bladder between an inner cloth that is to come into contact with the measurement site and an outer cloth that opposes the inner cloth, the band-shaped body being configured to be wrapped in a circumferential direction around the measurement site; and a plate member provided between the outer cloth and the air bladder in a thickness direction and in a region that corresponds to at least a portion in the circumferential direction of the band-shaped body, in which the thickness of the plate-shaped member gradually becomes thinner from the one side to the other side in an entire region of the plate member along the longitudinal direction.

In the present specification, "measurement site" refers to a site that can be wrapped with a cuff, such as a wrist or upper arm, in order to measure the blood pressure of a measurement subject. In particular, the measurement site at which the blood pressure measurement cuff of the present invention is worn is substantially in a round bar shape and gradually becomes thinner from one side to another side in the longitudinal direction.

Also, a "round bar shape" means a shape that extends in the longitudinal direction, has a cross section orthogonal to the longitudinal direction that is a circle, ellipse, oval, or a similar shape having a substantially round outline.

The band-shaped body "containing an air bladder" means that a substantial portion of an air bladder, or in other words, an air chamber, is contained in the band-shaped body.

Also, the "inner cloth" and "outer cloth" may be composed of a single layer or multiple layers of resin instead of cloth. In general, in order to compress the measurement site, the inner cloth has a high stretchability and the outer cloth is set to be substantially non-stretchable (or to have a lower stretchability compared to the inner cloth).

The blood pressure measurement cuff of the present invention is worn at a measurement site that extends in the longitudinal direction substantially in a round bar shape, and gradually becomes thinner from one side to another side in the longitudinal direction. In a state in which the cuff is being worn on the measurement site, the band-shaped body, which contains an air bladder between an inner cloth that is to be in contact with the measurement site and an outer cloth that opposes the inner cloth, is wrapped around the measurement site in the circumferential direction.

In this wearing state, if air is supplied to the cuff (or more accurately, to the air bladder) for blood pressure measurement, the air bladder is inflated, and the plate member provided between the outer cloth and the air bladder in the thickness direction receives an outward force from the air bladder. Along with that, the outer cloth receives an outward force.

As a result, the outer cloth starts to become a true circle in a cross section orthogonal to the longitudinal direction of the measurement site and remains parallel with the outer circumferential surface of the measurement site in a cross section taken along the longitudinal direction of the measurement site. Accompanying this, the surface of the outer cloth of the plate member becomes parallel with the outer circumferential surface of the measurement site in a cross section taken along the longitudinal direction of the measurement site. Here, the thickness of the plate member gradually becomes thinner from the one side to the other side in the entire region of the plate member along the longitudinal direction. Accordingly, the surface of the plate member on the air bladder side is parallel or almost parallel with the longitudinal direction of the measurement site rather than being parallel with the outer circumferential surface of the measurement site.

As a result, the outward force received by the plate member from the air bladder is substantially orthogonal or almost orthogonal to the longitudinal direction of the measurement site. Accordingly, the component of the outward force that is parallel to the longitudinal direction of the measurement site is eliminated or becomes smaller in comparison to the conventional example.

Similarly to the conventional example, the inner cloth receives an inward force from the air bladder. The inward force has a component that is parallel to the longitudinal direction. However, this component is canceled out by the friction force between the cuff (inner cloth) and the measurement site.

As a result, even if the air bladder is inflated, in actuality, the cuff no longer undergoes position shifting from the one side to the other side in the longitudinal direction. Also, due to the cuff no longer undergoing position shifting, compression loss stops occurring. Thus, with the blood pressure measurement cuff, the occurrence of position shifting and compression loss can be prevented.

With a blood pressure measurement cuff according to an embodiment, a degree to which the thickness of the plate member gradually becomes thinner from the one side to the other side in the longitudinal direction is set according to a degree to which the measurement site gradually becomes thinner from the one side to the other side in the longitudinal direction.

With the blood pressure measurement cuff according to the embodiment, the degree to which the thickness of the plate member gradually becomes thinner from the one side to the other side in the longitudinal direction is set according to the degree to which the measurement site gradually becomes thinner from the one side to the other side in the longitudinal direction. As a result, when the air bladder is inflated, the outward force received by the plate member from the air bladder becomes substantially orthogonal to the longitudinal direction of the measurement site. Accordingly, the component of the outward force that is parallel to the longitudinal direction of the measurement site is substantially eliminated. As a result, even if the air bladder is inflated, the cuff more reliably no longer undergoes position shifting.

With a blood pressure measurement cuff according to an embodiment,
the measurement site is a wrist, and
the plate member is provided so as to oppose only a region corresponding to a palm of a hand or a back of a hand in a circumference of the wrist.

In the present specification, "wrist" refers to a site near a hand that is on a terminus side with respect to the thickest portion of the forearm.

If the measurement site is a wrist, in a region corresponding to the palm of the hand or the back of the hand (referred to as "region corresponding to the palm of the hand" and "region corresponding to the back of the hand" as appropriate) in the circumference of the wrist, the degree of gradually becoming thinner from the one side to the other side in the longitudinal direction is larger in comparison to other regions. For this reason, it can be said that positional shifting and compression loss of the cuff are particularly likely to occur in the conventional example. Here, with the blood pressure measurement cuff according to this embodiment, the plate member is provided so as to oppose the region corresponding to the palm of the hand or the region corresponding to the back of the hand in the circumference of the wrist. Accordingly, the occurrence of position shifting and compression loss of the cuff can be effectively prevented. Also, the plate member is provided so as to oppose only the region corresponding to the palm of the hand or the region corresponding to the back of the hand (region having a large curvature radius) in the circumference of the wrist, and therefore when the cuff is worn by being wrapped around the wrist, the plate member does not become a hindrance by impairing the flexibility of the cuff. Accordingly, the cuff can be worn easily on the wrist.

With a blood pressure measurement cuff according to an embodiment, the plate member curves with a curvature radius that conforms to an outer circumferential surface of the region corresponding to the palm of the hand or the region corresponding to the back of the hand in the circumferential direction.

When the air bladder is inflated, the outer cloth starts to become a true circle in a cross-sectional view orthogonal to the longitudinal direction of the measurement site. If such a state continues, the thickness of the air layer in the air bladder (particularly, a portion adjacent to the region corresponding to the palm of the hand or the region corresponding to the back of the hand, which has a relatively large curvature radius) expands, the amount of air to be supplied to the air bladder increases, the load on the pump and the like increases. Here, with the blood pressure measurement cuff according to this embodiment, the plate member curves with a curvature radius that conforms to the outer circumferential surface of the region corresponding to the palm of the hand or the back of the hand (region having a relatively large curvature radius) in the circumferential direction. Accordingly, if the plate member is constituted by an elastic material that is difficult to bend compared to the outer cloth and the plate member is attached to the outer cloth, it is possible to suppress a case in which the outer cloth starts to become a true circle in a cross section orthogonal to the longitudinal direction of the measurement site. Also, the thickness of the air layer in the air bladder can be substantially reduced by an amount corresponding to the thickness of the plate member. As a result, the amount of air to be supplied to the air bladder can be reduced, whereby the load on the pump and the like can be reduced.

With a blood pressure measurement cuff according to an embodiment, the plate member is flat in the circumferential direction.

With the blood pressure measurement cuff according to this embodiment, the plate member is flat in the circumferential direction. Accordingly, the plate member can be manufactured more easily compared to the case in which the plate member curves in the circumferential direction, With a blood pressure measurement cuff according to an embodiment, a circumferential direction dimension of the plate member is constant from an end on the one side to an end on the other side in the longitudinal direction.

With the blood pressure measurement cuff according to this embodiment, the circumferential direction dimension of the plate member is constant from an end on the one side to an end on the other side in the longitudinal direction. Accordingly, the plate member can be manufactured more easily compared to the case in which the circumferential direction dimension of the plate member changes.

With a blood pressure measurement cuff according to an embodiment, a circumferential direction dimension of the plate member gradually decreases from the one side to the other side in the longitudinal direction.

With the blood pressure measurement cuff according to this embodiment, the circumferential direction dimension of the plate member gradually decreases from the one side to the other side in the longitudinal direction. Accordingly, the plate member easily fits within the outlines of the measurement site when the cuff worn on the measurement site is viewed from a side on which the plate member is provided. In such a case, a state is prevented in which the plate member projects past the outline of the measurement site and hampers the compression of the measurement site by the cuff. Accordingly, the cuff can be used to suitably compress an artery of the measurement site.

Also, if the circumferential direction dimension of the plate member gradually decreases from the one side to the other side in the longitudinal direction in this manner, it is easy to understand the orientation of attaching the plate member to the band-shaped body in a stage of assembling the cuff. That is, it is sufficient that the plate member is attached in an orientation in which the end of the plate member with a large circumferential direction dimension is on a side of the band-shaped body corresponding to the one side (thick side) of the measurement site in the wearing state, and the end of the plate member with a small circumferential direction dimension is on a side of the band-shaped body corresponding to the other side (thin side) of the measurement site in the wearing state. Accordingly, operational errors at the stage of assembling the cuff can be reduced.

With a blood pressure measurement cuff according to an embodiment, the plate member is composed of a material having elasticity.

With the blood pressure measurement cuff according to this embodiment, the plate member is composed of a material having elasticity. Accordingly, even if the plate member comes into contact with the measurement site via the inner cloth and the air bladder when the cuff is worn by being wrapped around the measurement site, there is little foreign object sensation and no pain is inflicted on the measurement subject.

In another aspect, a blood pressure monitor according to the present invention includes: the blood pressure measurement cuff; and a main body equipped with an element for blood pressure measurement.

In the present embodiment, an "element for blood pressure measurement" refers to a pump for supplying air to the air bladder of the cuff, a control unit for performing control for driving the pump, and the like.

The blood pressure monitor according to the present invention includes a blood pressure measurement cuff and a main body equipped with the element for blood pressure measurement. Accordingly, the occurrence of position shifting and compression loss of the cuff can be prevented.

With a blood pressure monitor according to an embodiment, the plate member of the cuff includes an element for coupling and integrating the cuff and the main body.

With the blood pressure monitor according to this embodiment, the plate member of the cuff includes an element for coupling and integrating the cuff and the main body. That is, the plate member fulfills two functions, namely a function of coupling and integrating the main body and the cuff, and a function of preventing the occurrence of position shifting and compression loss of the cuff. Accordingly, it is possible to prevent an increase in the number of parts in comparison with the case of using separate parts for these two functions.

Advantageous Effects of Invention

As is clear from the foregoing description, with the blood pressure measurement cuff according to the present invention, the occurrence of position shifting and compression loss can be prevented.

Also, with the blood pressure monitor according to the present invention, the occurrence of position shifting and compression loss of the cuff can be prevented.

DESCRIPTION OF EMBODIMENTS

Hereinafter, embodiments of the invention will be described in detail with reference to the drawings.

Figure 1:
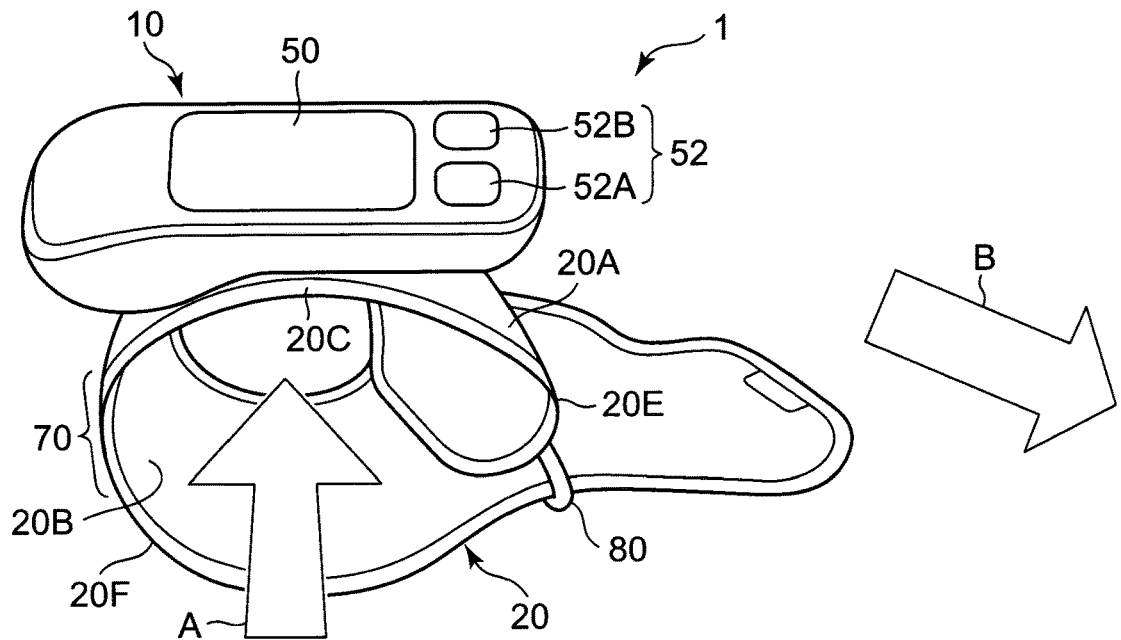
FIG. 1 is a perspective view showing the exterior of a blood pressure monitor having a blood pressure measurement cuff according to an embodiment of the present invention.
Figure 5:
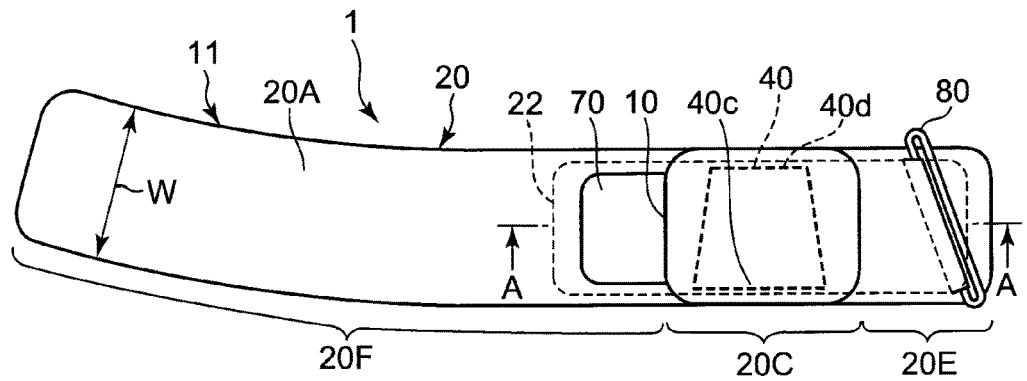
FIG. 5 is a diagram schematically showing a plan layout when the blood pressure monitor is viewed from a side on which a main body is provided in a state in which the cuff is unfolded.

FIG. 1 shows the exterior of a blood pressure monitor (indicated overall by reference numeral 1) according to an embodiment of the present invention. The blood pressure monitor 1 mainly has a blood pressure measurement cuff 20 that is to be wrapped around a wrist 90 (e.g., see FIG. 14) serving as a measurement site, and a main body 10 that is integrally attached to the cuff 20 and is equipped with an element for blood pressure measurement, FIG. 5 schematically shows a plan layout in a view of the blood pressure monitor 1 from a side on which the main body 10 is provided (corresponds to the outer circumferential side in FIG. 1), in a state in which the cuff 20 is unfolded. Also, FIG. 6 schematically shows a plan layout in a view of the blood pressure monitor 1 from a side opposite that of FIG. 5 (corresponds to the inner circumferential side in FIG. 1), in a state in which the cuff 20 is unfolded.

Figure 6:
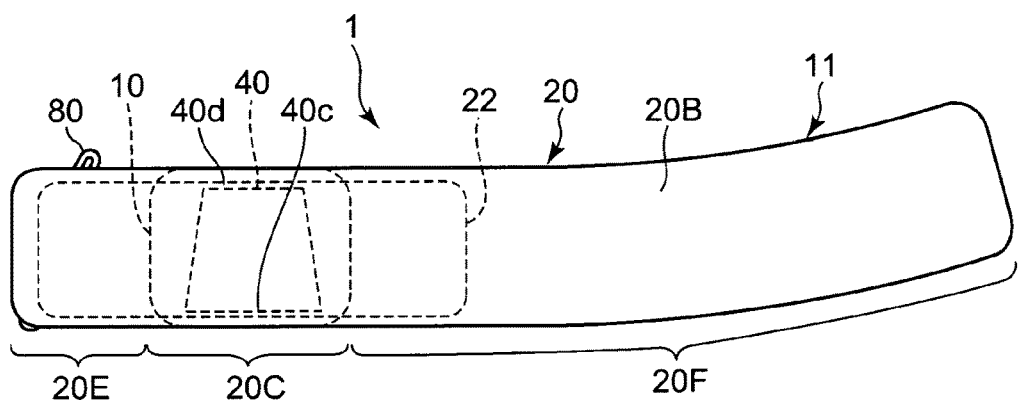
FIG. 6 is a diagram showing a plan layout when the blood pressure monitor is viewed from a side opposite that of FIG. 5, in a state in which the cuff is unfolded.

As is evident from FIGS. 5 and 6, the cuff 20 is formed as a bag-shaped band-shaped body 11 by sewing an outer cloth 20A and an inner cloth 20B together along the outer edges thereof. The inner cloth 20B is set to have high stretchability, and the outer cloth 20A is set to be substantially non-stretchable (or to have lower stretchability compared to the inner cloth 20B) so that it is easy to compress the measurement site.

In the longitudinal direction (corresponds to the circumferential direction in FIG. 1), the cuff 20 has a second portion 20C that conforms to the main body 10, a first portion 20E that extends from the second portion 20C to one side (the right side in FIG. 5), and a third portion 20F that extends from the second portion 20C to the other side (the left side in FIG. 5).

The third portion 20F curves so as to be downwardly convex in FIGS. 5 and 6. The orientation of the curvature was set under the assumption that, in FIGS. 5 and 6, the cuff 20 wraps around and is worn on the wrist 90 in a mode in which the elbow side (wider side) 90e of the wrist 90 is located downward and the hand side (narrower side) 90f of the wrist 90 is located upward.

A ring 80 having a substantially oval shape is attached to the outer circumferential surface of the first portion 20E. The longitudinal direction of the ring 80 intersects with the longitudinal direction of the cuff 20. The dimension in the longitudinal direction of the ring 80 is set to be slightly larger than the width direction dimension W of the cuff 20 so that the cuff 20 (particularly the third portion 20F) can be easily passed through.

A surface fastener 70 is attached to the surface of a proximal portion near the main body 10 of the third portion 20F of the cuff 20. In this example, the surface fastener 70 has many small hooks (not shown) on its surface. The outer circumferential surface of the portion other than the proximal portion (surface fastener 70) of the third portion 20F has many small loops (not shown) that engage with the hooks.

Figure 7:
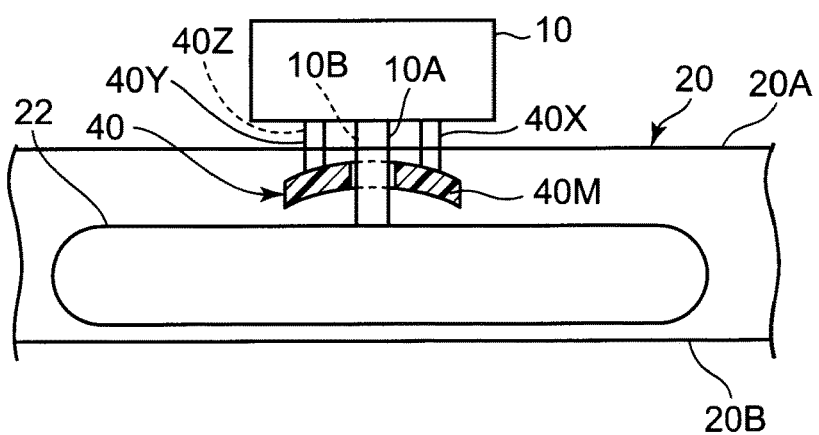
FIG. 7 is a diagram schematically showing a cross section taken along line A-A in FIG. 5.

The cuff 20 contains an air bladder 22 for compressing the wrist 90, spanning from the first portion 20E to the third portion 20F. Also, as shown in FIG. 7 (corresponds to a cross-section taken along line A-A in FIG. 5), a plate member 40 is inserted in the thickness direction between the outer cloth 20A and the air bladder 22 in the second portion 20C. The plate member 40 joins and integrates the main body 10 and the cuff 20, and functions to prevent the occurrence of position shifting and compression loss of the cuff 20 (to be described in detail later).

Figure 10:
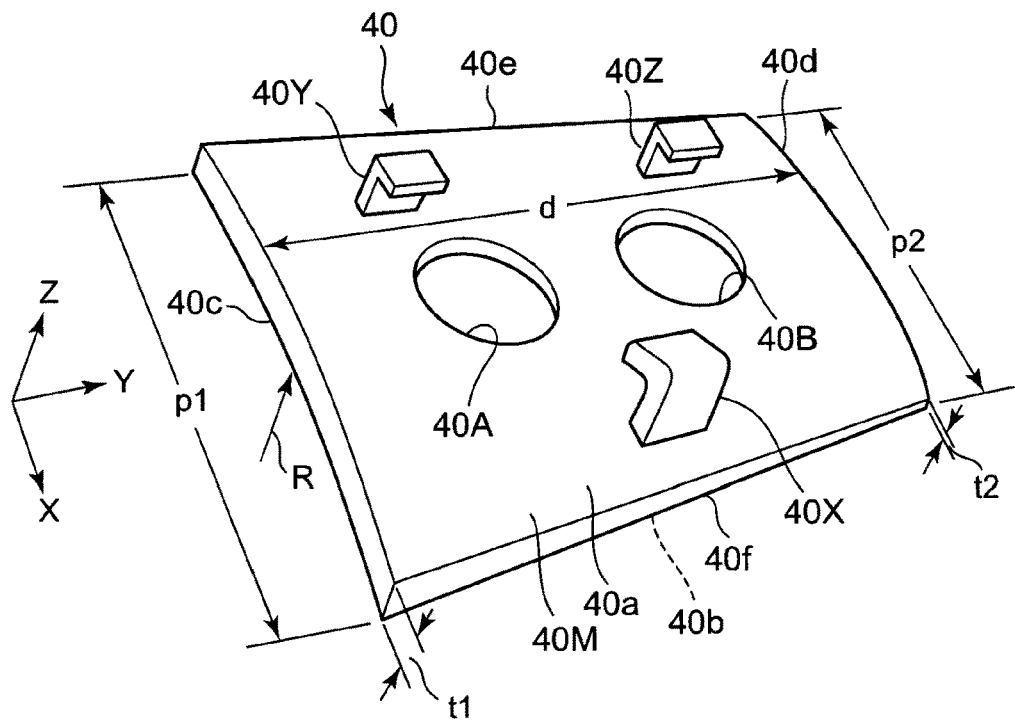
FIG. 10 is a diagram showing a perspective view of an exemplary plate member included in the cuff

FIG. 10 shows a perspective view of a single plate member 40. Note that FIG. 10 shows an XYZ orthogonal coordinate system as well in order to facilitate understanding (the same applies to FIGS. 11 to 14). The X direction corresponds to the circumferential direction of the cuff shown in FIG. 1. The Y direction corresponds to the width direction of the cuff (corresponds to the longitudinal direction of the measurement site). The Z direction corresponds to the thickness direction of the cuff The plate member 40 includes a plate-shaped main portion 40M, and hooks 40X, 40Y, and 40Z that are formed on one surface (upper surface in FIG. 10) 40a of the main portion 40M. The upper surface 40a of the main portion 40M shown in FIG. 10 corresponds to the surface that is to be attached to the inner surface of the outer cloth 20A, and the lower surface 40b corresponds to the surface that is to oppose the outer circumferential surface of the wrist 90 via the air bladder 22. The plate member 40 is composed of a plastic material (in this example, ABS (acrylonitrile-butadiene-styrene copolymer) resin), and is formed integrally by extrusion molding. The plastic material of the plate member 40 has an elasticity that makes it more difficult to bend compared to the outer cloth 20A.

In this example, the main portion 40M has a substantially trapezoidal outline in a view in the Z direction. A dimension p2 of a +Y-side side 40d is set to be smaller than a dimension p1 of a −Y-side side 40c. Two inclined sides (±X-side sides) 40e and 40f are set to be symmetrical to each other. As a result, the dimension in the X direction (corresponds to circumferential direction of the wrist 90 serving as the measurement site) of the main portion 40M gradually decreases from the −Y side to the +Y side (i.e., from the elbow side 90e to the hand side 90f in FIG. 15). In this example, the dimension p1 is set to be about several cm (e.g., within a range of 3 to 8 cm) in accordance with the width of the wrist of an average person. The dimension p2 is set to be about 1 cm smaller than the dimension p1 (e.g., 0.5 cm to 2 cm). A dimension d between the side 40c and the side 40d is set to be within a range of about several cm to 10 cm, for example.

The main portion 40M curves with a constant curvature radius R (upwardly convex in FIG. 10) so as to conform with the outer circumferential surface that the wrist 90 is to oppose. In this example, the curvature radius R of the main portion 40M is set to be around several cm (e.g., within a range of 3 cm to 10 cm) according to the curvature radius of the wrist of an average person (a later-described region 90a corresponding to the palm of the hand, or a region 90b corresponding to the back of the hand).

Figure 15:
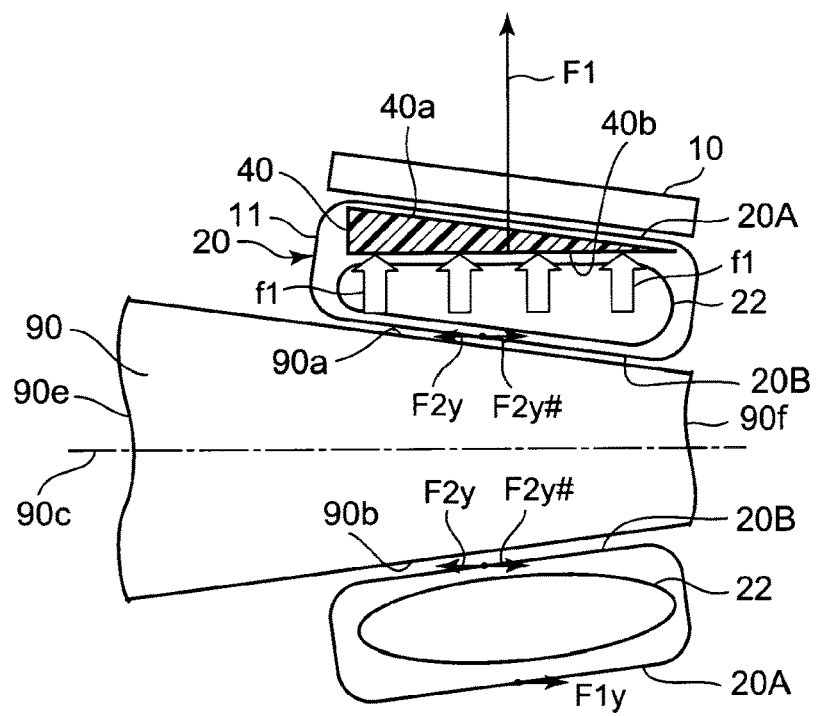
FIG. 15 is a longitudinal cross-sectional view schematically showing a situation during measurement, in which the cuff including the plate member shown in FIG. 10 is worn on the wrist along with the main body.

The thickness of the main portion 40M gradually decreases with a constant gradient in this example from the −Y side to the +Y side (i.e., from the elbow side 90e to the hand side 90f in FIG. 15). In this example, the thickness t1 of the −Y-side side 40c is set to be 3 mm, and the thickness t2 of the +Y-side side 40d is set to be 1 mm. The degree to which the thickness of the plate member 40 (main portion 40M) gradually becomes thinner from the −Y side to the +Y side in the longitudinal direction 90c is set according to the degree to which the wrist 90 of an average person gradually becomes thinner from the elbow side 90e to the hand side 90f. That is, the difference between the thickness t1 of the side 40c and the thickness t2 of the side 40d (2 mm in this example) corresponds to the fact that the radius of the wrist 90 of an average person decreases by about 2 mm between the side 40c and the side 40d (dimension d).

On the main portion 40M, two circular through holes 40A and 40B are provided in alignment in the Y direction at an approximately central position in the X direction. These through holes 40A and 40B are used to pass air pipes (described later) through which the main body 10 and the air bladder 22 of the cuff 20 are in communication.

A hook 40X is provided frontward (on the +X side) with respect to the through holes 40A and 40B in the X direction, and at an intermediate position between the through holes 40A and 40B in the Y direction on one surface (the upper surface shown in FIG. 10) of the main portion 40M. Hooks 40Y and 40Z are provided at positions that are rearward (on the −X side) with respect to the through holes 40A and 40B in the X direction, and slightly outward (toward the −Y and +Y sides) with respect to the through holes 40A and 40B in the Y direction. The hooks 40X, 40Y, and 40Z stick out from the one surface of the main portion 40M. The tip of the hook 40X is bent toward the −X side, whereas the tips of the hooks 40Y and 40Z are bent toward the +X side. The hooks 40X, 40Y, and 40Z are used as elements for coupling and integrating the main body 10 and the cuff 20.

Figure 8:
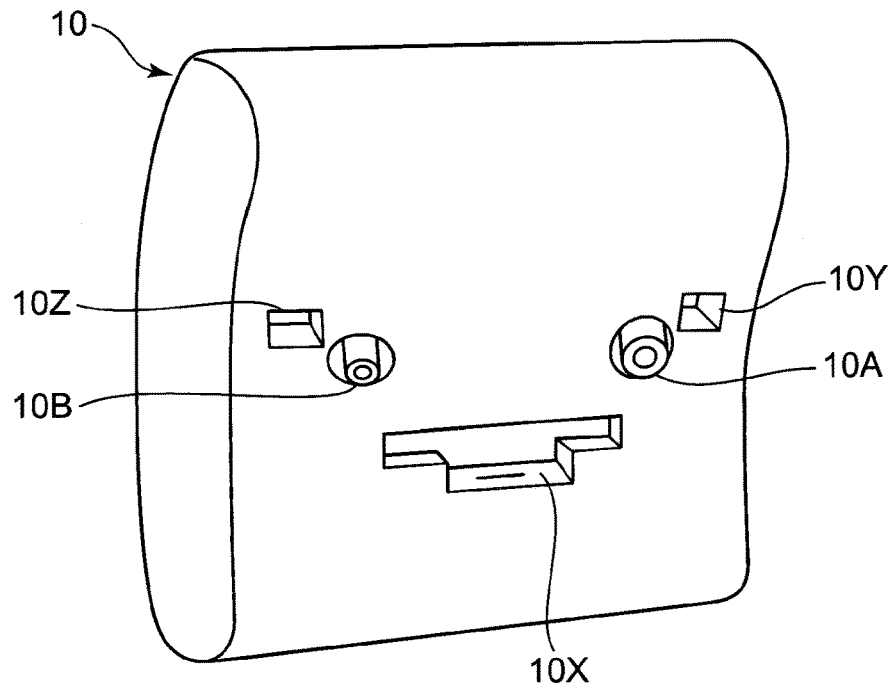
FIG. 8 is a diagram showing elements on a main body side for coupling the main body and the cuff of the blood pressure monitor.
Figure 9:
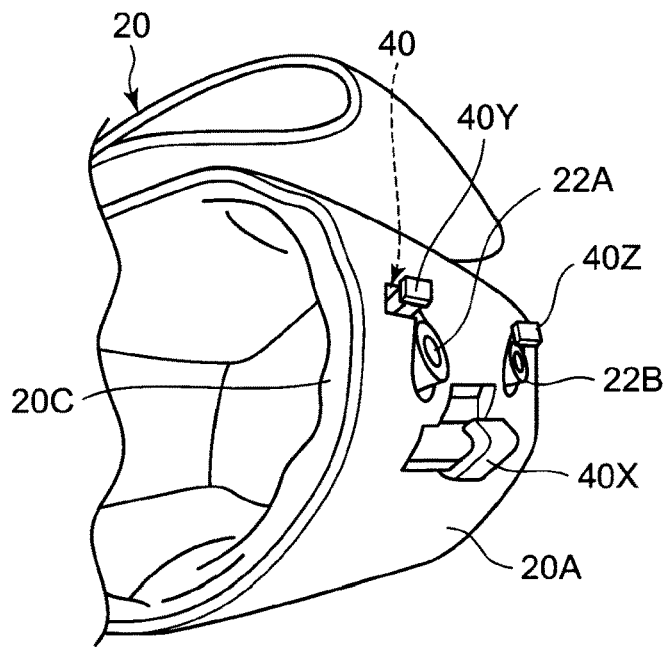
FIG. 9 is a diagram showing elements on a cuff side for joining the main body and the cuff of the blood pressure monitor.

As shown in FIG. 8, on the surface of the main body 10 opposing the cuff 20 (lower surface in FIG. 1), air pipes 10A and 10B that are to be in communication with the air bladder 22 of the cuff 20 are provided, and holes 10X, 10Y, and 10Z for coupling the main body 10 to the cuff 20 are formed. On the other hand, in a second portion 20C of the cuff 20, nipple tubes 22A and 22B that are continuous with the air bladder 22 are exposed and the hooks 40X, 40Y, and 40Z of the plate member 40 are exposed through openings provided in the outer cloth 20A. The hook-side surface of the main portion 40M of the plate member 40 (upper surface 40a shown in FIG. 10) is attached to the inner surface of the outer cloth 20A using double-sided adhesive tape (not shown), for example.

When the main body 10 and the cuff 20 are coupled, the hooks 40X, 40Y, and 40Z of the plate member 40 are positioned so as to engage with the holes 10X, 10Y, and 10Z of the main body 10. Along with that, the air pipes 10A and 10B of the main body 10 fit air-tightly into nipple tubes 22A and 22B that are continuous with the air bladder 22. In this manner, as shown in FIGS. 1 and 7, the main body 10 and the cuff 20 are coupled and integrated.

Figure 3:
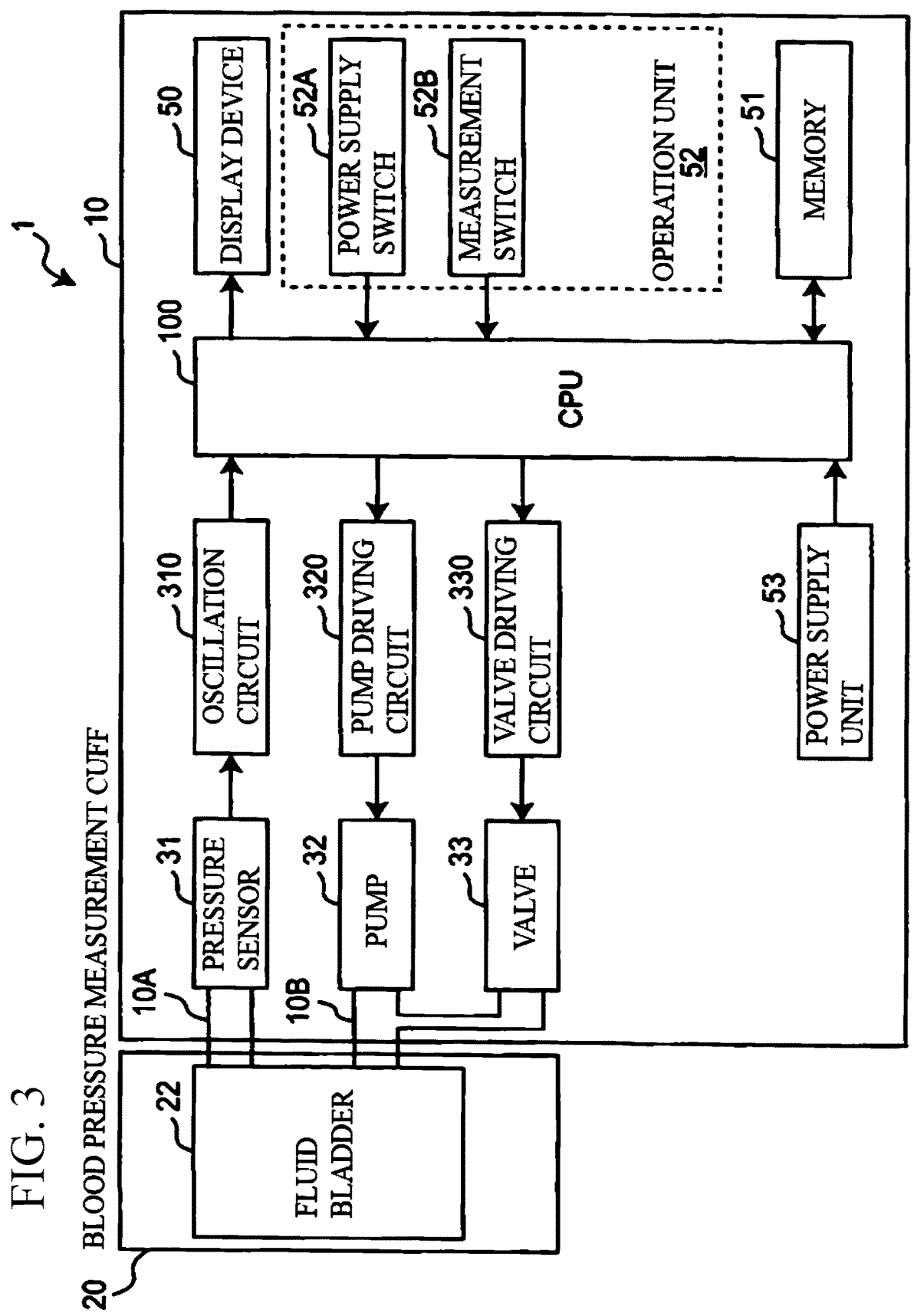
FIG. 3 is a diagram showing a schematic block configuration of the blood pressure monitor.

FIG. 3 shows a schematic block configuration of the cuff 20 and the main body 10 of the blood pressure monitor 1. The blood pressure monitor 1 includes a CPU (Central Processing Unit) 100 serving as a control unit, a display device 50, a memory 51 serving as a storage unit, an operation unit 52, a power supply unit 53, a pump 32, a valve 33, and a pressure sensor 31, all of which are mounted in the main body 10. Also, the main body 10 includes an oscillation circuit 310 that converts the output from the pressure sensor 31 into a frequency, a pump driving circuit 320 that drives the pump 32, and a valve driving circuit 330 that drives the valve 33, all of which are mounted in the main body 10.

The display device 50 includes a display, an indicator, and the like, and displays predetermined information in accordance with a control signal from the CPU 100.

The operation unit 52 includes a power supply switch 52A that receives input of an instruction for turning the power supply unit 53 on or off, and a measurement switch 52B for receiving an instruction for starting blood pressure measurement. The switches 52A and 52B input operation signals corresponding to instructions given by the user to the CPU 100.

The memory 51 stores data of programs for controlling the blood pressure monitor 1, data to be used for controlling the blood pressure monitor 1, setting data for setting various functions of the blood pressure monitor 1, data of blood pressure value measurement results, and the like. Also, the memory 51 is used as a work memory or the like for when a program is executed.

In accordance with a program that is stored in the memory 51 and is for controlling the blood pressure monitor 1, the CPU 100 performs control for driving the pump 32 and the valve 33 according to operation signals from the operation unit 52. Also, the CPU 100 calculates blood pressure values and controls the display device 50 and the memory 51 based on the signal from the pressure sensor 31.

The power supply unit 53 supplies power to the units, namely the CPU 100, the pressure sensor 31, the pump 32, the valve 33, the display device 50, the memory 51, the oscillation circuit 310, the pump driving circuit 320, and the valve driving circuit 330.

The pump 32 supplies air to the air bladder 22 in order to increase the pressure (cuff pressure) in the air bladder 22 contained in the cuff 20. The valve 33 opens and closes in order to discharge or seal the air in the air bladder 22, whereby the cuff pressure is controlled. The pump driving circuit 320 drives the pump 32 based on a control signal obtained from the CPU 100. The valve driving circuit 330 opens and closes the valve 33 based on a control signal obtained from the CPU 100.

The pressure sensor 31 and the oscillation circuit 310 function as a pressure detection unit that detects the pressure of the cuff. The pressure sensor 31 (e.g., a piezoresistive pressure sensor) is connected via the air pipe 10A to the air bladder 22 contained in the cuff 20, and the pump 32 and the valve 33 are connected via the air pipe 10B to the air bladder 22 contained in the cuff 20. In this example, the oscillation circuit 310 oscillates based on an electric signal value that is based on a change in electric resistance caused by the piezoresistant effect from the pressure sensor 31, and outputs a frequency signal having a frequency corresponding to the electric signal value of the pressure sensor 31 to the CPU 100.

Figure 2:
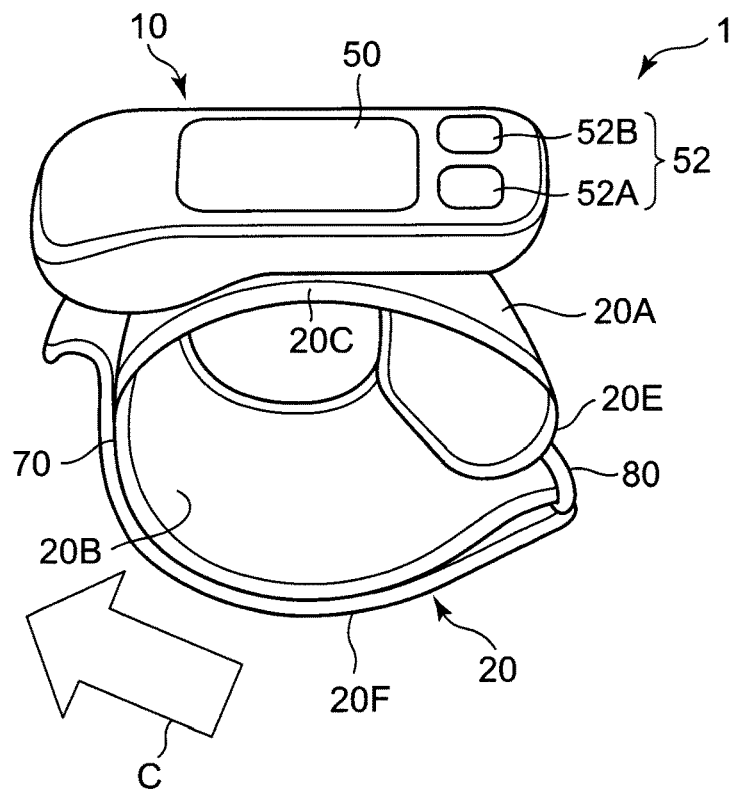
FIG. 2 is a perspective view showing a state when the blood pressure monitor is worn on a measurement site (not shown).

When the blood pressure monitor 1 (cuff 20) is to be worn on the wrist 90 serving as the measurement site, as indicated by the arrow A in FIG. 1, the wrist 90 is passed through the middle of the cuff 20 with the palm of the hand facing upward, and the second portion 20C of the cuff 20 is placed on the wrist 90, along with the main body 10. Next, the portion of the third portion 20F of the cuff 20 that is located far from the main body 10 is passed through the ring 80, is pulled diagonally downward to the right as indicated by the arrow B in FIG. 1, and is folded back on itself as indicated by the arrow C in FIG. 2. Then, the folded-back portion is fixed by being pressed onto a surface fastener 70.

Here, the plate member 40 (e.g., see FIG. 7) is composed of a material having elasticity, as described above. Accordingly, even if the plate member 40 comes into contact with the wrist 90 via the inner cloth 20B and the air bladder 22 when the cuff 20 is worn by being wrapped around the wrist 90, there is little foreign object sensation and no pain is inflicted on the measurement subject.

Figure 4:
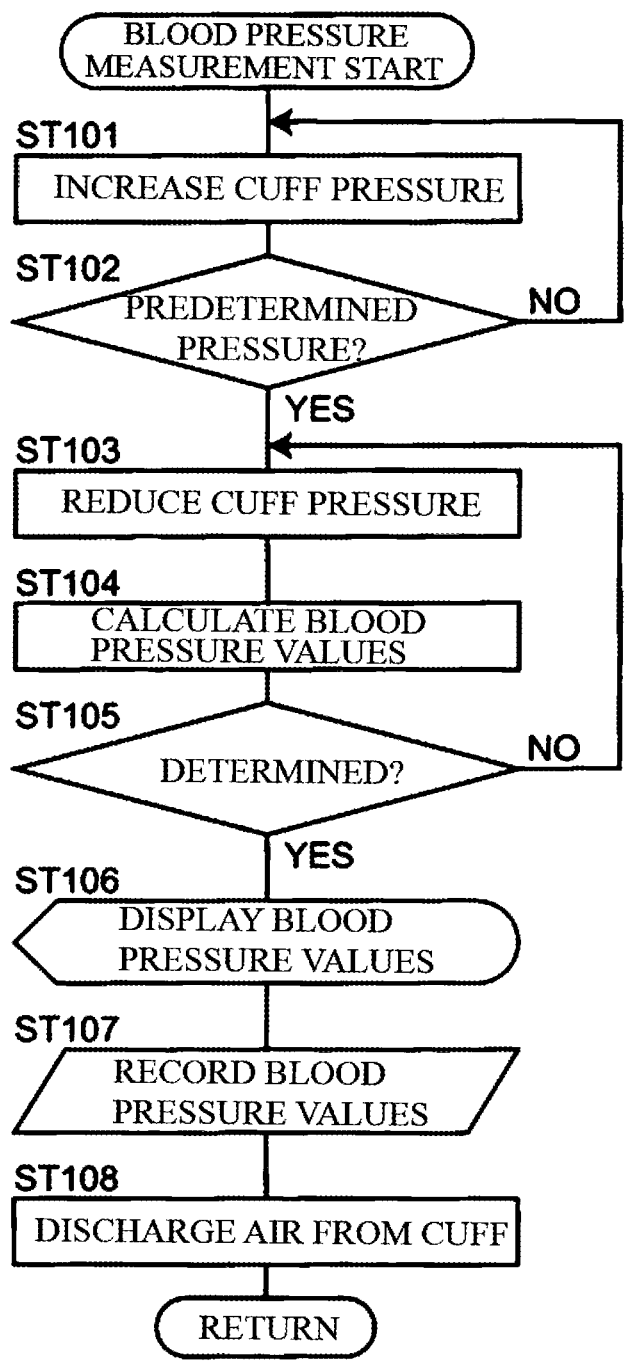
FIG. 4 is a diagram showing an operation flow of the blood pressure monitor.

With the blood pressure meter 1, blood pressure values of a test subject are measured by the CPU 100 using an oscillometric method in accordance with the flow shown in FIG. 4.

Specifically, when the measurement switch 52B is pressed while the power supply switch 52A is turned on, the blood pressure monitor 1 starts blood pressure measurement as shown in FIG. 4. At the start of blood pressure measurement, the CPU 100 initializes the memory region for processing and outputs a control signal to the valve driving circuit 330. The valve driving circuit 330 discharges the air in the air bladder 22 of the cuff 20 by opening the valve 33 based on the control signal. Next, control for adjusting the pressure sensor 31 to 0 mmHg is performed.

Upon starting blood pressure measurement, first, the CPU 100 performs control for closing the valve 33 via the valve driving circuit 330, and thereafter driving the pump 32 via the pump driving circuit 320 so as to send air to the air bladder 22. According to this, the air bladder 22 is inflated and the cuff pressure gradually increases (step ST101).

When the cuff pressure is increased to a predetermined pressure (YES in step ST102), the CPU 100 performs control for stopping the pump 32 via the pump driving circuit 320 and thereafter gradually opening the valve 33 via the valve driving circuit 330. According to this, the air bladder 22 is deflated and the cuff pressure gradually decreases (step ST103).

Here, the predetermined pressure is a pressure that is sufficiently higher than the systolic blood pressure of the measurement subject (e.g., systolic blood pressure+30 mmHg), and is stored in advance in the memory 51, or is determined by the CPU 100 estimating the systolic blood pressure using a predetermined calculation equation while the cuff pressure is increased (e.g., see JP 2001-70263A).

Also, regarding the pressure decrease rate, a target pressure decrease rate that is to be a target is set while the cuff is being inflated, and the CPU 100 controls the degree of opening of the valve 33 so as to reach the target pressure decrease rate.

In the pressure decrease process, via the cuff 20, the pressure sensor 31 detects a cuff pressure signal (indicated by reference numeral Pc) indicating the pressure of the cuff 20. Based on the cuff pressure signal Pc, the CPU 100 calculates the blood pressure values (systolic blood pressure and diastolic blood pressure) by applying a later-described algorithm using the oscillometric method (step ST104). Note that the calculation of the blood pressure values is not limited to the pressure decrease process, and may be calculated in the pressure increase process.

Upon calculating and determining the blood pressure values (YES in step ST105), the CPU 100 performs control for displaying the calculated blood pressure values on the display device 50 (step ST106) and storing the blood pressure values in the memory 51 (step ST107).

When the measurement ends, the CPU 100 performs control for opening the valve 33 via the valve driving circuit 330 and discharging the air in the air bladder 22 of the cuff 20 (step ST108).

Figure 14:
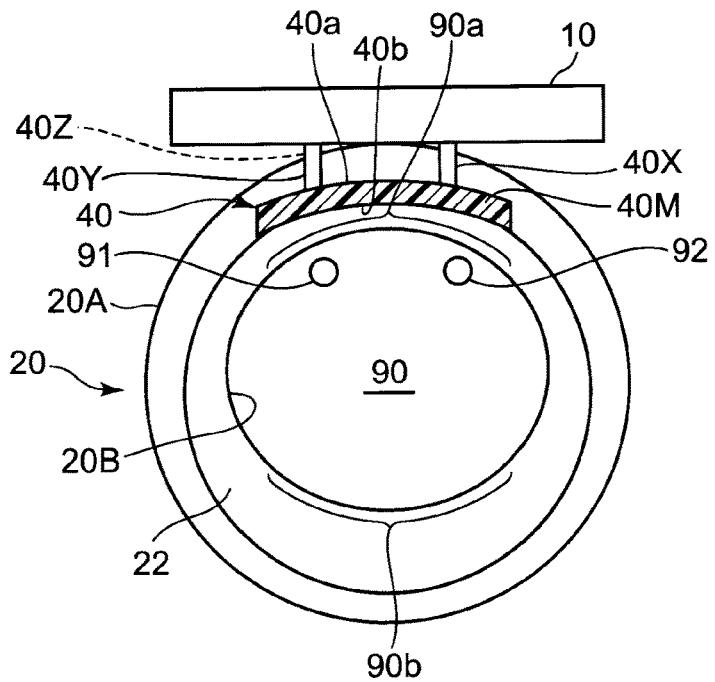
FIG. 14 is a lateral cross-sectional view schematically showing a situation during measurement, in which the cuff including the plate member shown in FIG. 10 is worn on the wrist along with the main body.

FIGS. 14 and 15 schematically show a state during measurement in which the blood pressure monitor 1 (cuff 20) is worn on the wrist 90. FIG. 14 shows a cross section (lateral cross-section) orthogonal to the longitudinal direction of the wrist 90, and FIG. 15 shows a cross section (longitudinal cross section) taken along the longitudinal direction 90c of the wrist. Note that in FIGS. 14 and 15, illustration of the air pipes 10A and 10B is omitted for the sake of simplicity. As shown in FIG. 14, the cross section of the wrist 90 is approximately elliptical (or oval). The region 90a corresponding to the palm of the hand and the region 90b corresponding to the back of the hand in the circumference of the wrist 90 have curvature radii that are larger in comparison to those of other regions. Note that in FIG. 14, a ○ mark 91 shown in the wrist 90 indicates a radial artery, and a ○ mark 92 indicates an ulnar artery.

In this example, the main body 10 and the plate member 40 (particularly the main portion 40M) of the blood pressure monitor 1 oppose the region 90a corresponding to the palm of the hand in the circumference of the wrist 90. As shown in FIG. 15, the wrist 90 has an approximate round bar shape and gradually becomes thinner from the elbow side (one side) 90e to the hand side (other side) 90f in the longitudinal direction 90c.

When air is supplied to the cuff 20 (or more accurately, to the air bladder 22) in order to perform blood pressure measurement in the wearing state, the air bladder 22 is inflated, and the plate member 40 provided between the outer cloth 20A and the air bladder 22 in the thickness direction receives outward forces f1, f1, . . . from the air bladder 22, as shown in FIG. 15. Reference numeral F1 indicates a combined force obtained by combining the outward forces f1, f1, . . . . Along with this, the outer cloth 20A receives the outward force F1.

As a result, the outer cloth 20A starts to become a true circle in the lateral cross section shown in FIG. 14, and remains parallel with the outer circumferential surface of the wrist 90 in the longitudinal cross section shown in FIG. 15. Accompanying this, the surface 40a on the outer cloth side of the plate member 40 is parallel with the outer circumferential surface of the wrist 90 in the longitudinal cross section shown in FIG. 15, Here, the thickness of the plate member 40 gradually becomes thinner in the entire region from the elbow side 90e to the hand side 90f. Accordingly, the surface 40b on the air bladder side of the plate member 40 is parallel or almost parallel with the longitudinal direction (center) 90c of the wrist 90 rather than being parallel with the outer circumferential surface of the wrist 90.

As a result, as shown in FIG. 15, the outward force F1 received by the plate member 40 from the air bladder 22 is orthogonal or almost orthogonal to the longitudinal direction 90c of the wrist 90. Accordingly, the component of the outward force F1 that is parallel to the longitudinal direction 90c of the wrist 90 (F1y shown in FIG. 23) is eliminated or decreases in comparison to the conventional example (for this reason, F1y is not shown in FIG. 15), In this example, the inner cloth 20B receives an inward force (F2 shown in FIG. 23) from the air bladder 22, similarly to the conventional example. The inward force F2 has a component F2y that is parallel to the longitudinal direction 90c, as shown in FIG. 15. However, the component F2y is canceled out by a friction force F2y# between the cuff 20 (inner cloth 20B) and the wrist 90.

As a result, even if the air bladder 22 is inflated, in actuality, the cuff 20 will no longer undergo position shifting from the elbow side 90e to the hand side 90f. Also, due to the cuff 20 no longer undergoing positional shifting, compression loss also no longer occurs. Thus, with the cuff 20, the occurrence of position shifting and compression loss can be prevented.

Figure 23:
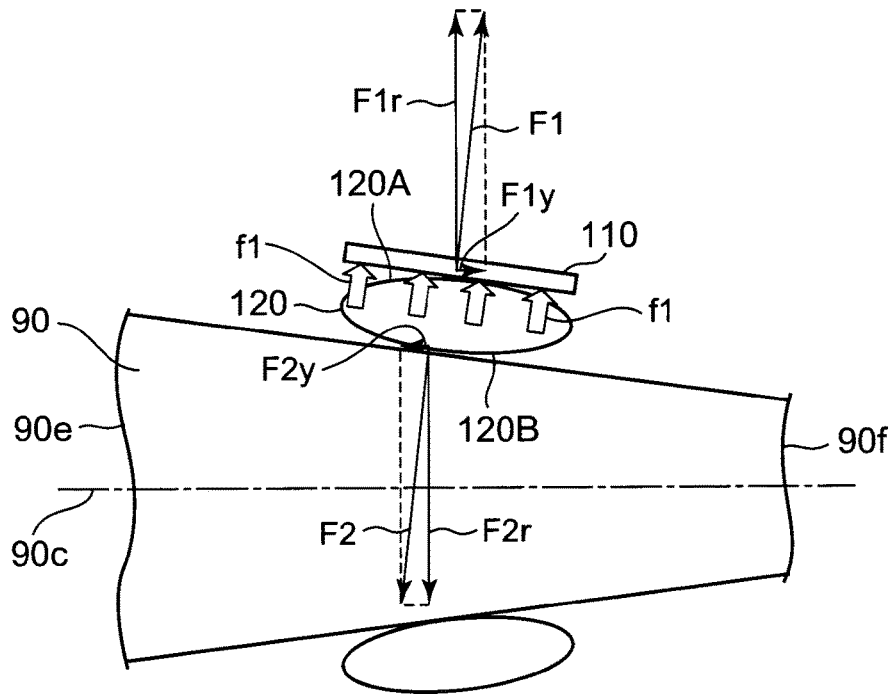
FIG. 23 is a diagram for describing a problem of position shifting in a conventional blood pressure measurement cuff
Figure 24:
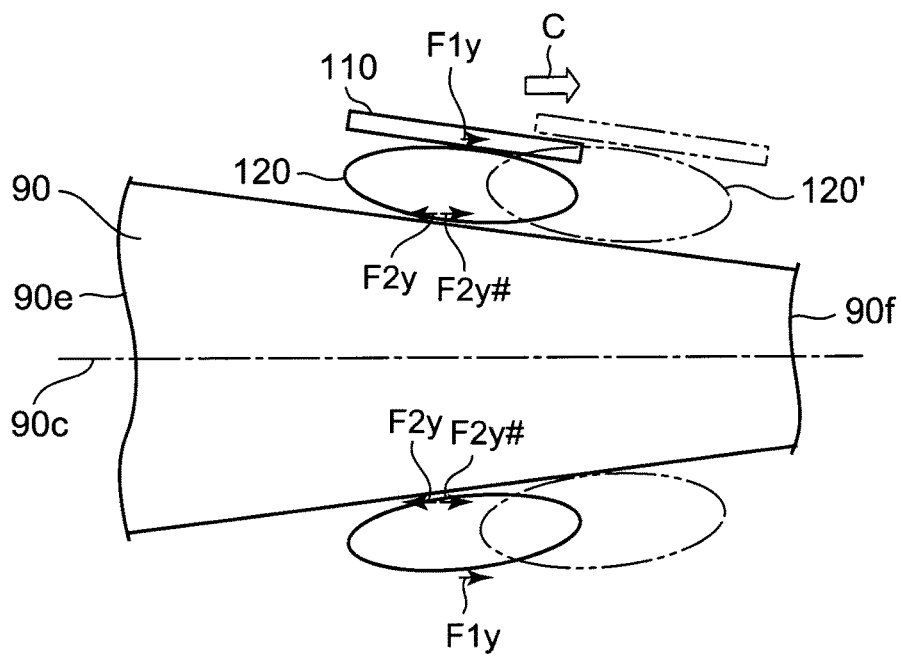
FIG. 24 is a diagram for describing a problem of position shifting in a conventional blood pressure measurement cuff.

Note that in a region in which the plate member 40 is not provided in the circumference of the wrist 90 (in this example, the region 90b corresponding to the back of the hand), the outer cloth 20A receives an outward force F1 that is inclined toward the hand side 90f with respect to the longitudinal direction 90c of the wrist, similarly to the conventional example (see FIG. 23). Also, the inner cloth 20B receives the inward force F2 that is inclined toward the elbow side 90e with respect to the longitudinal direction 90c of the wrist. However, in the region in which the plate member 40 is provided in the circumference of the wrist 90 (in this example, the region 90a corresponding to the palm of the hand), position shifting of the cuff 20 is suppressed, and therefore, in actuality, the cuff 20 no longer undergoes position shifting with respect to the measurement site (wrist 90).

In particular, in the above example, the degree to which the thickness of the plate member 40 (main portion 40M) gradually becomes thinner from the −Y side to the +Y side is set according to the degree to which the wrist 90 of an average person gradually becomes thinner from the elbow side to the hand side. As a result, when the air bladder 22 is inflated, the outward force F1 received by the plate member 40 from the air bladder 22 is substantially orthogonal to the longitudinal direction 90c of the wrist 90. Accordingly, the component F1y (see FIG. 23) of the outward force F1 that is parallel with the longitudinal direction 90c of the wrist 90 is substantially eliminated. As a result, even if the air bladder 22 is inflated, the cuff 20 more reliably no longer undergoes position shifting.

Also, if the measurement site is the wrist 90, in the region 90a corresponding to the palm of the hand and the region 90b corresponding to the back of the hand in the circumference of the wrist 90, the degree of gradually becoming thinner from the elbow side 90e to the hand side 90f is large compared to other regions. For this reason, it can be said that positional shifting and compression loss of the cuff are particularly likely to occur in the conventional example.

Here, in this example, the plate member 40 is provided so as to oppose the region 90a corresponding to the palm of the hand in the circumference of the wrist 90. Accordingly, the occurrence of position shifting and compression loss of the cuff 20 can be effectively prevented. Also, the plate member 40 is provided so as to oppose only the region 90a corresponding to the palm of the hand in the circumference of the wrist 90 (a region with a relatively large curvature radius), and therefore when the cuff 20 is worn by being wrapped in the circumferential direction of the wrist 90, the plate member 40 does not cause a hindrance by impairing the flexibility of the cuff 20. Accordingly, the cuff 20 can be worn easily on the wrist 90.

Also, when the air bladder 22 is inflated, the outer cloth 20A starts to become a true circle in the lateral cross section shown in FIG. 14. If this state continues, the thickness of the air layer in the air bladder 22 (particularly, the portions adjacent to the region 90a corresponding to the palm of the hand and the region 90b corresponding to the back of the hand, which have a relatively larger curvature radius) expands, the amount of air to be supplied to the air bladder 22 increases, and the load on the pump and the like increases. Here, with the cuff 20, the plate member 40 curves with a curvature radius R that conforms to the outer circumferential surface of the region 90a corresponding to the palm of the hand, which has a relatively large curvature radius, in the circumference of the wrist 90. Also, the plate member 40 is constituted by an elastic material that is difficult to bend compared to the outer cloth 20A, and the plate member 40 is in contact with the outer cloth 20A. Accordingly, it is possible to suppress a case in which the outer cloth 20A starts to become a true circle in the lateral cross section shown in FIG. 14. Also, the thickness of the air layer in the air bladder 22 can be substantially reduced by an amount corresponding to the thickness of the plate member 40. As a result, the amount of air to be supplied to the air bladder 22 can be reduced, whereby the load on the pump and the like can be reduced.

Figure 21:
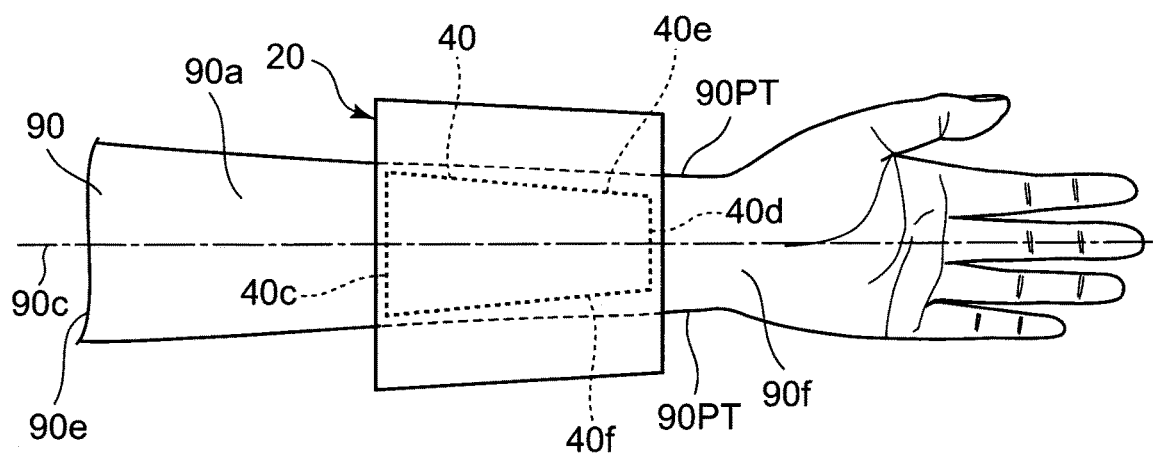
FIG. 21 is a diagram schematically showing a situation in a view from a side on which the plate member is provided, when the cuff including the plate member shown in FIG. 10 is worn on the wrist.

Also, with the cuff 20, the circumferential direction dimension (corresponds to X direction dimension in FIG. 10) of the plate member 40 (main portion 40M) gradually decreases from the elbow side 90e to the hand side 90f in FIG. 15. Accordingly, the plate member 40 easily fits within outlines 90PT and 90PT of the wrist 90 when the cuff 20 worn on the wrist 90 is viewed from a side on which the plate member 40 is provided, as shown in FIG. 21. In such a case, a circumstance is prevented in which the plate member 40 projects past the outline 90PT of the wrist 90 and hinders compression of the wrist 90 by the cuff 20. Accordingly, the cuff 20 can be used to suitably compress an artery of the wrist 90.

Also, if the circumferential direction dimension (corresponding to the X direction dimension shown in FIG. 10) of the plate member 40 (main portion 40M) gradually decreases from the elbow side 90e to the hand side 90f in this manner, the orientation in which the plate member 40 is attached to the band-shaped body 11 is easy to find out in the stage of assembling the cuff 20. That is, in FIGS. 5 and 6, it is sufficient that the plate member 40 is attached in an orientation in which the side 40c, at which the circumferential direction dimension of the plate member 40 is large, is on a side (lower side in FIGS. 5 and 6) of the band-shaped body 11 corresponding to the elbow side (thick side) 90e of the wrist 90 in the wearing state, and the side 40d, at which the circumferential direction dimension of the plate member 40 is small, is on a side (upper side in FIGS. 5 and 6) of the band-shaped body 11 corresponding to the hand side (thin side) 90f of the wrist 90 in the wearing state. Accordingly, operational errors at the stage of assembling the cuff 20 can be reduced.

Also, in this example, the plate member 40 carries out two functions, namely coupling and integrating the main body 10 and the cuff 20, and preventing the occurrence of position shifting and compression loss of the cuff 20. Accordingly, it is possible to prevent an increase in the number of parts in comparison with the case of using separate parts for these two functions.

Variation 1

Figure 16:
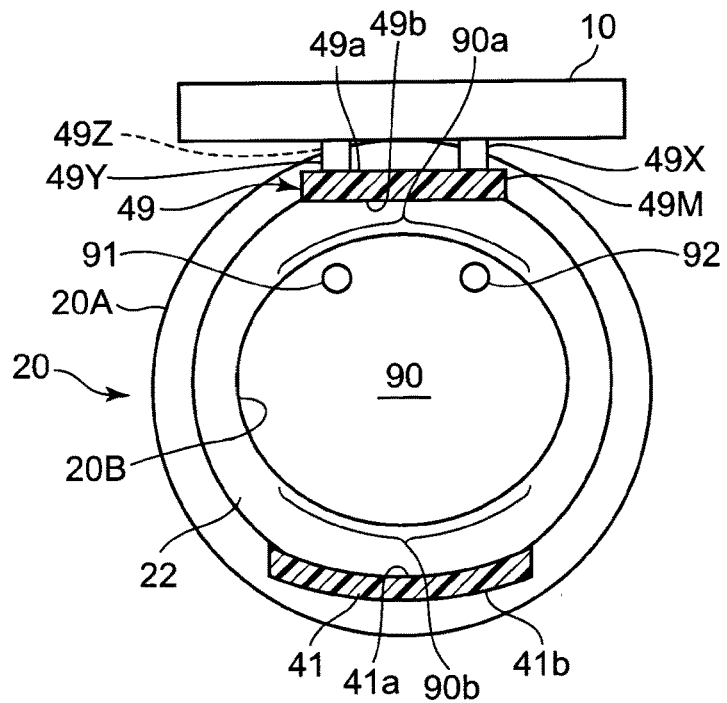
FIG. 16 is a lateral cross-sectional view schematically showing a situation during measurement, in which the cuff including the plate member shown in FIG. 11 is worn on the wrist along with the main body.

In the foregoing example, the plate member 40 was provided in order to carry out two functions, namely coupling and integrating the main body 10 and the cuff 20, and preventing the occurrence of position shifting and compression loss of the cuff 20, but there is no limitation to this. As shown in FIG. 16 for example, it is possible to provide a coupling plate 49 exclusively for coupling the main body 10 and the cuff 20 at the region 90a corresponding to the palm of the hand while providing a plate member 41 exclusively for preventing position shifting of the cuff 20 at the region 90b corresponding to the back of the hand.

The coupling plate 49 includes a main portion 49M with a flat (compressed parallelepiped) shape with a constant thickness, and hooks 49X, 49Y, and 49Z that are formed on one surface (upper surface in FIG. 16) 49a of the main portion 49M. The upper surface 49a of the main portion 49M shown in FIG. 16 is attached to the inner surface of the outer cloth 20A and the lower surface 49b opposes the outer circumferential surface of the wrist 90 via the air bladder 22. The configuration and arrangement of the hooks 49X, 49Y, and 49Z are similar to those of the plate member 40 in the above example. The hooks 49X, 49Y, and 49Z of the coupling plate 49 are positioned so as to respectively engage with holes 10X, 10Y, and 10Z of the main body 10. Accordingly, the main body 10 and the cuff 20 are coupled. Note that similarly to the above example, the air pipes 10A and 10B exist between the main body 10 and the air bladder 22, but in FIG. 16, illustration thereof is omitted for the sake of simplicity (the same applies to FIGS. 17 to 20).

Figure 11:
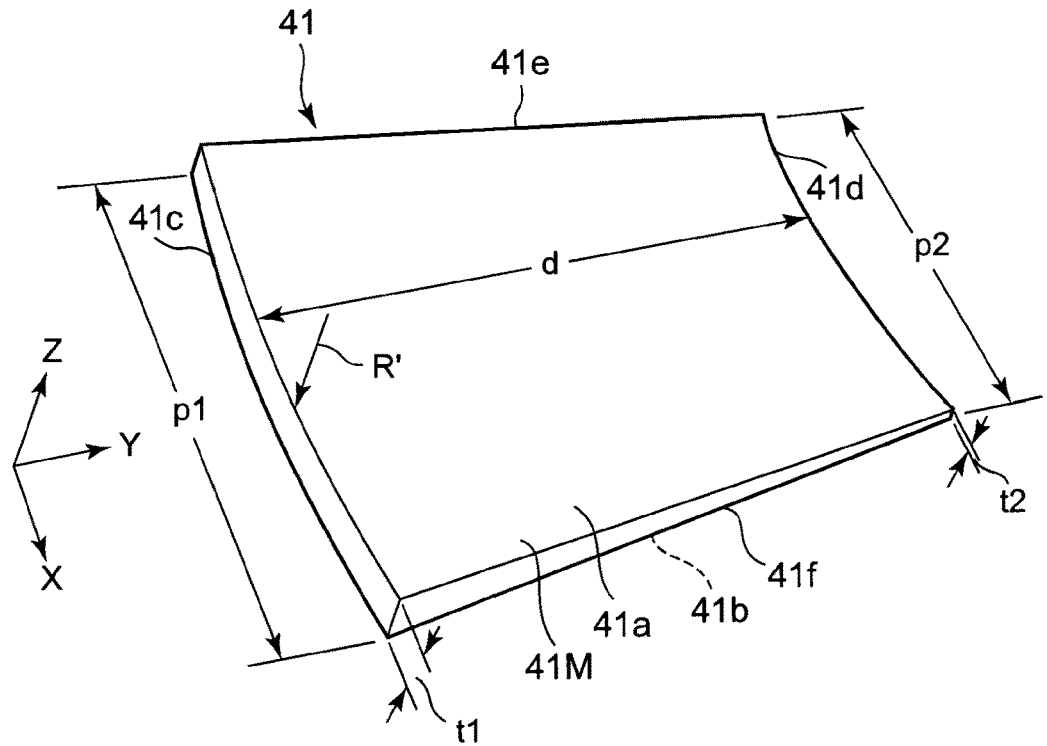
FIG. 11 is a diagram showing a perspective view of another exemplary plate member included in the cuff.

As shown in FIG. 11, the plate member 41 is composed of a plate-shaped main portion 41M that is approximately vertically symmetrical with the main portion 40M of the plate member 40 shown in FIG. 10. The upper surface 41a of the main portion 41M shown in FIG. 10 corresponds to the surface that is to oppose the outer circumferential surface of the wrist 90 via the air bladder 22 and the inner cloth 20B, and the lower surface 41b corresponds to the surface that is to be attached to the inner surface of the outer cloth 20A. The plate member 41 is exclusively for preventing position shifting of the cuff 20, and therefore does not include hooks or through holes. The plate member 41 (main portion 41M) is composed of a plastic material (in this example, ABS (acrylonitrile-butadiene-styrene copolymer) resin) having an elasticity that makes it more difficult to bend compared to the outer cloth 20A.

The main portion 41M has a substantially trapezoidal outline, which is the same as that of the main portion 40M of the plate member 40, in a view in the Z direction. The dimension p1 of the side 41c, the dimension p2 of the side 41d, and the dimensions of the two inclined sides 41e and 41f are set to be the same as the dimensions of the main portion 40M of the plate member 40.

The main portion 41M curves with a constant curvature radius R' (downwardly convex in FIG. 11) so as to conform with the outer circumferential surface that the wrist 90 is to oppose. In this example, the curvature radius R' (absolute value) of the main portion 41M is set to be the same as the curvature radius R of the main portion 40M of the plate member 40, The thickness of the main portion 41M gradually (in this example, at a constant gradient) becomes thinner from the −Y side to the +Y side. In this example, the thickness t1 of the −Y-side side 41c and the thickness t2 of the +Y-side side 41d are set to be the same as in the main portion 40M of the plate member 40.

As shown in FIG. 16, when air is supplied to the cuff 20 (or more accurately, to the air bladder 22) in order to perform blood pressure measurement while the blood pressure monitor 1 (cuff 20) is worn on the wrist 90, in the region in which the plate member 41 is not provided in the circumference of the wrist 90 (in this example, the region 90a corresponding to the palm of the hand, or the like), the outer cloth 20A receives an outward force F1 that is inclined toward the hand side 90f with respect to the longitudinal direction 90c of the wrist, similarly to the conventional example (see FIG. 23). Also, the inner cloth 20B receives the inward force F2 that is inclined toward the elbow side 90e with respect to the longitudinal direction 90c of the wrist. However, in the region in which the plate member 41 is provided in the circumference of the wrist 90 (in this example, the region 90b corresponding to the back of the hand), position shifting of the cuff 20 is suppressed, and therefore, in actuality, the cuff 20 no longer undergoes position shifting from the elbow side 90e to the hand side 90f. Also, due to the cuff 20 no longer undergoing positional shifting, compression loss also no longer occurs. Accordingly, the occurrence of position shifting and compression loss of the cuff 20 can be prevented, similarly to the previous example.

Also, in this example, the plate member 41 is provided so as to oppose the region 90b corresponding to the back of the hand in the circumference of the wrist 90 (the degree to which the measurement site gradually becomes thinner from the elbow side 90e to the hand side 90f is large). Accordingly, the occurrence of position shifting and compression loss of the cuff 20 can be effectively prevented similarly to the case in the previous example in which the plate member 41 was provided so as to oppose the region 90a corresponding to the palm of the hand. Also, the plate member 41 is provided so as to oppose only the region 90b corresponding to the back of the hand in the circumference of the wrist 90 (a region with a relatively large curvature radius), and therefore when the cuff 20 is worn by being wrapped in the circumferential direction of the wrist 90, the plate member 40 does not cause a hindrance by impairing the flexibility of the cuff 20. Accordingly, the cuff 20 can be worn easily.

Here, with the cuff 20, the plate member 41 curves with a curvature radius R' that conforms to the outer circumferential surface of the region 90b corresponding to the back of the hand, which has a relatively large curvature radius, in the circumference of the wrist 90. Also, the plate member 41 is constituted by an elastic material that is difficult to bend compared to the outer cloth 20A, and the plate member 41 is in contact with the outer cloth 20A. Accordingly, it is possible to suppress a state in which the outer cloth 20A becomes a true circle in the cross section (cross section orthogonal to the longitudinal direction 90c of the wrist 90) shown in FIG. 11. Also, the thickness of the air layer in the air bladder 22 can be substantially reduced by an amount corresponding to the thickness of the plate member 41. As a result, the amount of air to be supplied to the air bladder 22 can be reduced, whereby the load on the pump and the like can be reduced.

Also, similarly to the plate member 40 of the previous example shown in FIG. 21, the plate member 41 easily fits within the outlines 90PT and 90PT of the wrist in a view of the wrist 90 from a side on which the plate member 41 is provided. In such a case, a circumstance is prevented in which the plate member 41 projects past the outline 90PT of the wrist 90 and hinders compression of the wrist 90 by the cuff 20. Accordingly, the cuff 20 can be used to suitably compress an artery of the wrist 90.

Also, if the circumferential direction dimension (corresponds to the X direction dimension shown in FIG. 11) of the plate member 41 (main portion 41M) gradually decreases from the one side 90e to the other side 90f in this manner, the orientation in which the plate member 41 is attached to the band-shaped body 11 is easy to find out in the stage of assembling the cuff 20. That is, in FIGS. 5 and 6, it is sufficient that the plate member 41 is attached in an orientation in which the side 41c, at which the circumferential direction dimension of the plate member 41 is large, is on a side (lower side in FIGS. 5 and 6) of the band-shaped body 11 corresponding to the elbow side (thick side) 90e of the wrist 90 in the wearing state, and the side 41d, at which the circumferential direction dimension of the plate member 41 is small, is on a side (upper side in FIGS. 5 and 6) of the band-shaped body 11 corresponding to the hand side (thin side) 90f of the wrist 90 in the wearing state. Accordingly, operational errors at the stage of assembling the cuff 20 can be reduced.

Variation 2

Figure 17:
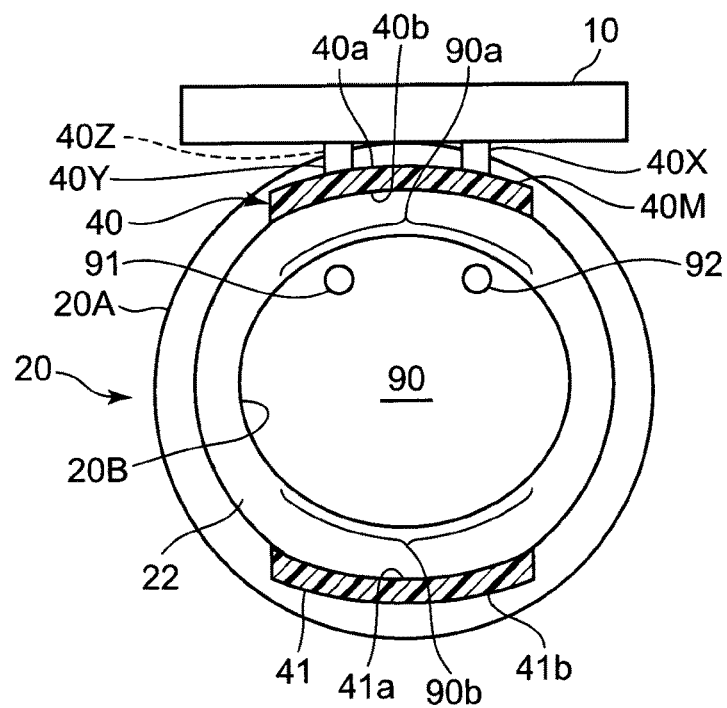
FIG. 17 is a lateral cross-sectional view schematically showing a situation during measurement, in which the cuff including both the plate member shown in FIG. 10 and the plate member shown in FIG. 11 is worn on the wrist along with the main body.

In each of the above examples (the examples shown in FIGS. 14 and 16), one plate member with a thickness that gradually became thinner from the elbow side 90e to the hand side 90f was provided, but there is no limitation thereto. For example, as shown in FIG. 17, it is possible to provide the plate member 40 in the region 90a corresponding to the palm of the hand and provide the plate member 41 in the region 90b corresponding to the back of the hand. The plate members 40 and 41 were described with reference to FIGS. 10 and 11 respectively.

Figure 18:
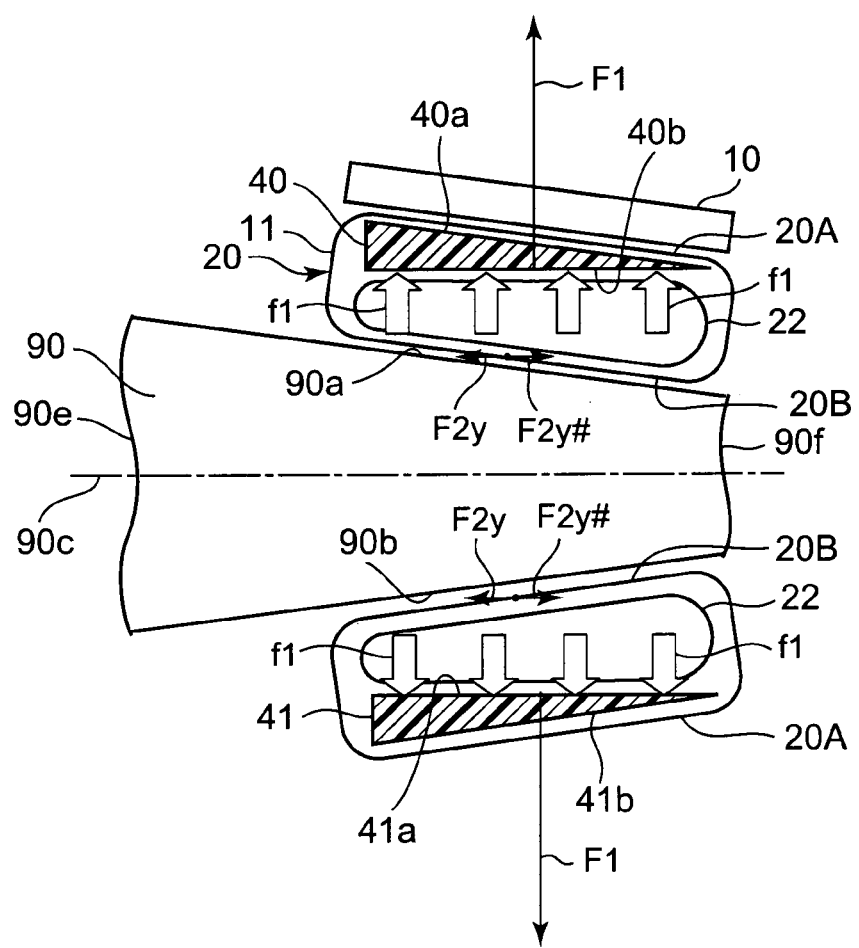
FIG. 18 is a longitudinal cross-sectional view schematically showing a situation during measurement, in which the cuff including both the plate member shown in FIG. 10 and the plate member shown in FIG. 11 is worn on the wrist along with the main body.

As shown in FIG. 17, when air is supplied to the cuff 20 (or more accurately, to the air bladder 22) in order to perform blood pressure measurement while the blood pressure monitor 1 (cuff 20) is worn on the wrist 90, the air bladder 22 is inflated, and the plate member 40 provided in the region 90a corresponding to the palm of the hand and the plate member 41 provided in the region 90b corresponding to the back of the hand receive outward forces f1, f1, . . . from the air bladder 22, as shown in FIG. 18. Reference numeral F1 indicates a combined force obtained by combining the outward forces f1, f1, . . . .

Because the thicknesses of the main portions 40M and 41M of the plate members 40 and 41 gradually become thinner from the elbow side 90e to the hand side 90f, the outward force F1 received by the plate members 40 and 41 from the air bladder 22 is orthogonal or almost orthogonal to the longitudinal direction 90c of the wrist 90. Accordingly, the component of the outward force F1 that is parallel to the longitudinal direction 90c of the wrist 90 (F1y shown in FIG. 23) is eliminated or decreases in comparison to the conventional example (for this reason, F1y is not shown in FIG. 18). Accordingly, in this example, the force that starts to cause the cuff 20 to move from the elbow side 90e to the hand side 90f can be removed in both the region 90a corresponding to the palm of the hand and the region 90b corresponding to the back of the hand.

Also, in this example, the inner cloth 20B receives an inward force (F2 shown in FIG. 23) from the air bladder 22, similarly to the conventional example. The inward force F2 has a component F2y that is parallel with the longitudinal direction 90c, as shown in FIG. 18. However, the component F2y is canceled out by a friction force F2y# between the cuff 20 (inner cloth 20B) and the wrist 90.

As a result, it is possible to more reliably prevent the cuff 20 from undergoing position shifting from the elbow side 90e to the hand side 90f. Also, due to the cuff 20 no longer undergoing positional shifting, compression loss also no longer occurs. Thus, according to this example, the occurrence of position shifting and compression loss can be reliably prevented.

Variation 3

The above-described plate members 40 and 41 were curved so as to conform to the outer circumferential surface that the measurement site (wrist 90) is to oppose, but there is no limitation thereto.

Figure 12:
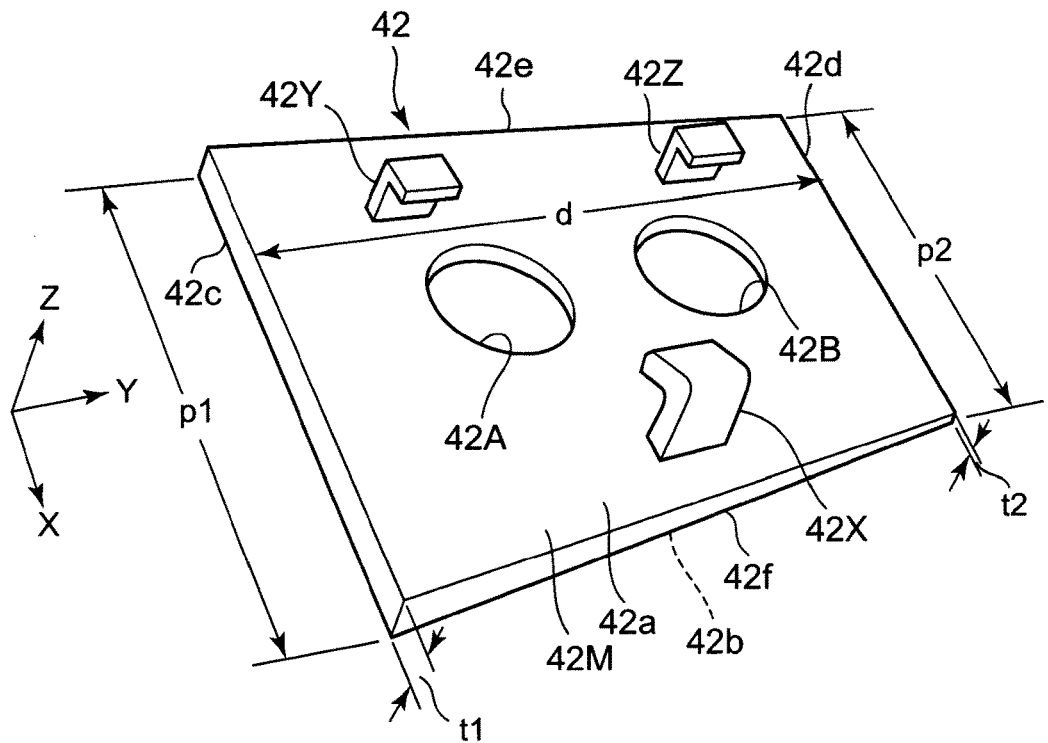
FIG. 12 is a diagram showing a perspective view of yet another exemplary plate member included in the cuff.
Figure 19:
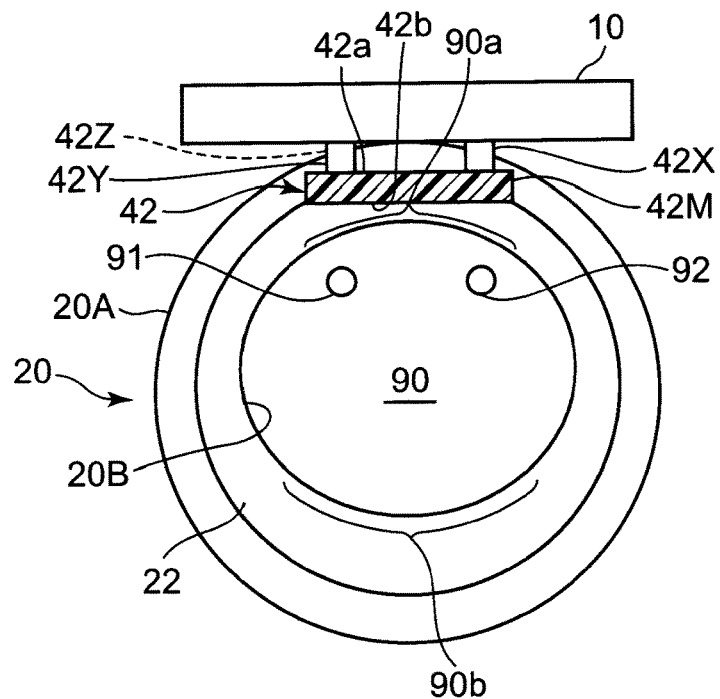
FIG. 19 is a lateral cross-sectional view schematically showing a situation during measurement, in which the cuff including the plate member shown in FIG. 12 is worn on the wrist along with the main body.

For example, as shown in FIG. 12, it is possible to use a plate member 42 that is flat in the circumferential direction (corresponds to the X direction in FIG. 12) of the measurement site (wrist 90). Regarding the reference numerals of the elements shown in FIG. 12, reference numeral 40, which was included in the reference numerals of the elements shown in FIG. 10, has been changed to 42. Accordingly, redundant description is not included. Note that FIG. 19 schematically shows a lateral side view of a state in which the cuff 20, which includes the plate member 42, is worn on the wrist 90.

The configuration of the plate member 42 is the same as the configuration of the plate member 40 shown in FIG. 10, except that the plate member 42 is flat in the X direction. In particular, the thickness of the main portion 42M of the plate member 42 gradually becomes thinner from the −Y side in FIG. 12 to the +Y side (i.e., from the elbow side 90e in FIG. 15 to the hand side 90f). Accordingly, it is possible to prevent the cuff 20 from undergoing position shifting from the elbow side 90e to the hand side 90f. Also, the plate member 42 can be manufactured more easily compared to the case where the plate member curves in the circumferential direction.

Variation 4

The circumferential direction dimensions of the above-described plate members 40, 41, and 42 gradually became thinner from the −Y side in FIGS. 10 to 12 to the +Y side (i.e., from the elbow side 90e in FIG. 15 to the hand side 90f), but there is no limitation to this.

Figure 13:
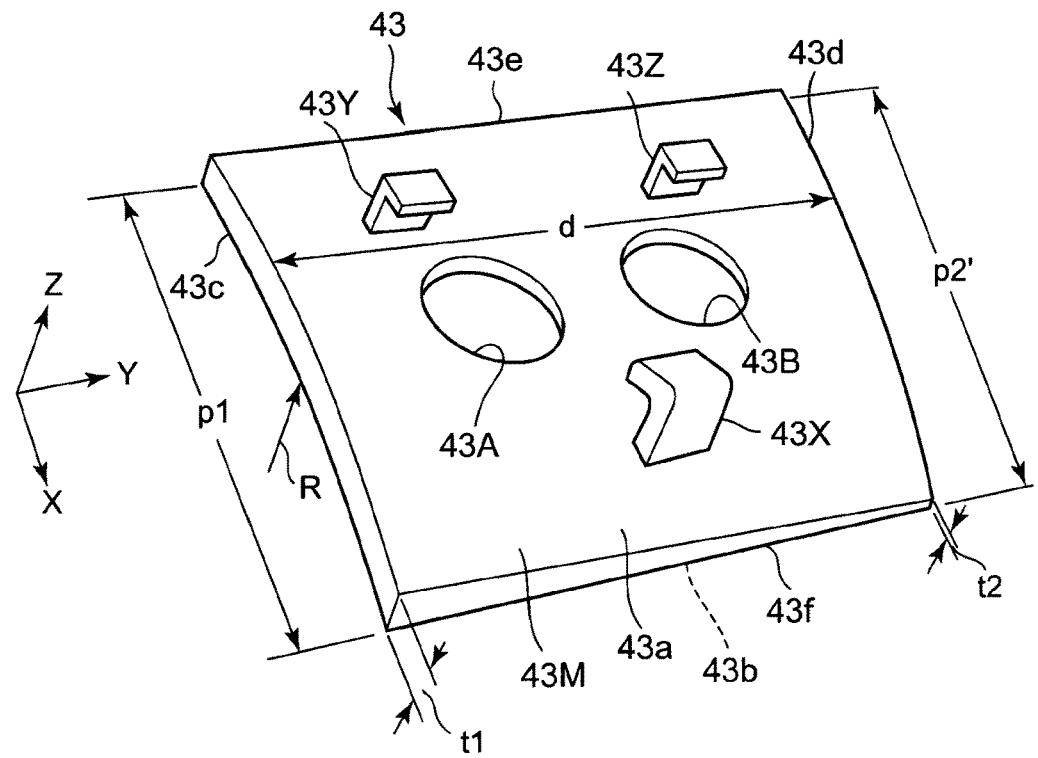
FIG. 13 is a diagram showing a perspective view of yet another exemplary plate member included in the cuff.
Figure 20:
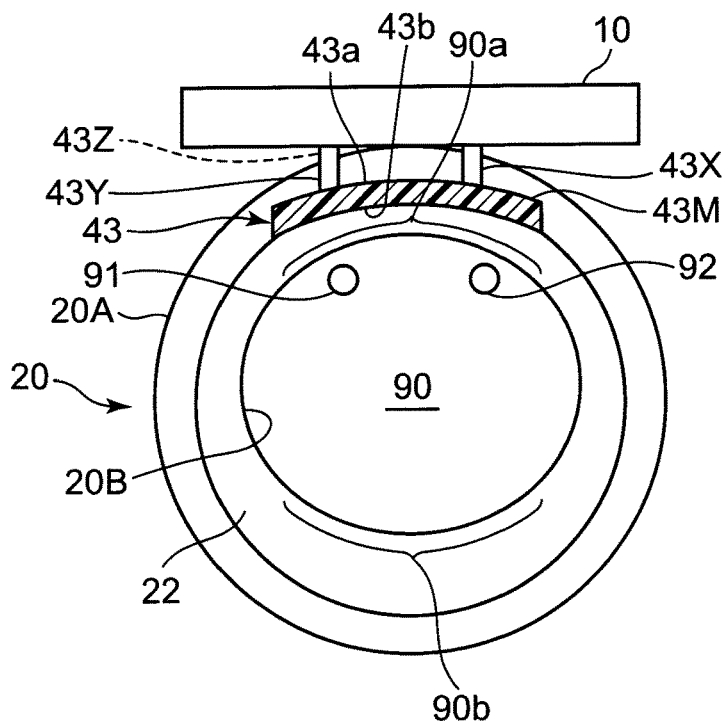
FIG. 20 is a lateral cross-sectional view schematically showing a situation during measurement, in which the cuff including the plate member shown in FIG. 13 is worn on the wrist along with the main body.
Figure 22:
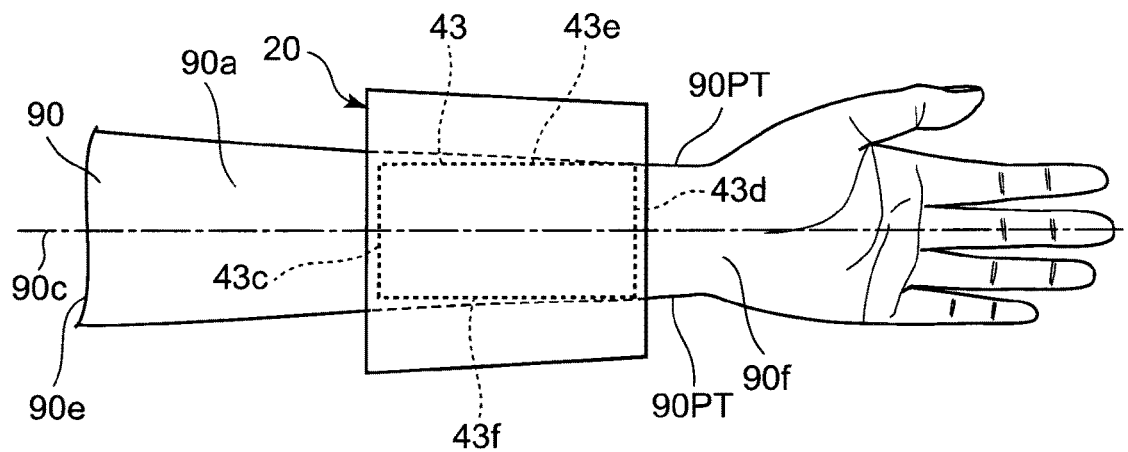
FIG. 22 is a diagram schematically showing a situation in a view from a side on which the plate member is provided, when the cuff including the plate member shown in FIG. 13 is worn on the wrist.

For example, as shown in FIG. 13, the circumferential direction dimension of the plate member 43 may be constant from the −Y-side side 43c in FIG. 13 to the +Y-side side 43d. That is, the dimension p1 of the −Y-side side 43c and a dimension p2' of the +Y-side side 43d may be equal. Regarding the reference numerals of the elements shown in FIG. 13, reference numeral 40, which was included in the reference numerals of the elements shown in FIG. 10, has been changed to 43. Accordingly, redundant description is not included. Note that FIG. 20 schematically shows a lateral side view of a state in which the cuff 20, which includes the plate member 43, is worn on the wrist 90. Also, FIG. 22 schematically shows a situation viewed from a side on which the plate member 43 is provided, in a state in which the cuff 20, which includes the plate member 43, is worn on the wrist 90.

The configuration of the plate member 43 is the same as the configuration of the plate member 40 shown in FIG. 10, except that the circumferential direction dimension of the plate member 43 is constant. In particular, the thickness of the main portion 43M of the plate member 43 gradually becomes thinner from the −Y side to the +Y side (i.e., from the elbow side 90e in FIG. 22 to the hand side 90f). Accordingly, it is possible to prevent the cuff 20 from undergoing position shifting from the elbow side 90e to the hand side 90f. Also, the plate member 43 can be more easily manufactured compared to the case in which the circumferential direction dimension of the plate member gradually becomes thinner from the elbow side 90e to the hand side 90f.

Note that it is possible to integrate an element of the above-described plate member 42 into the plate member 43 and use a configuration of the plate member 43 that is flat in the circumferential direction of the measurement site (wrist 90). In such a case, the plate member 43 can be manufactured even more easily.

In the above examples, the material of the plate members 40, 41, 42, and 43 was a plastic material having elasticity (e.g., ABS resin), but there is no limitation to this. For example, rubber or elastomer may be used as the material of the plate member.

The above-described embodiments are exemplary and can be modified in various ways without departing from the scope of the invention. The above-described multiple embodiments can be achieved separately, and it is also possible to combine embodiments. Also, the various characteristics of the different embodiments can be achieved separately, and it is also possible to combine characteristics of different embodiments.

REFERENCE SIGNS LIST

1 Blood pressure monitor
10 Main body
20 Cuff
40, 41, 42, 43 Plate member
49 Coupling plate

The invention claimed is:

1. A blood pressure measurement cuff to be worn on a measurement site on a subject's arm, the measurement site extending in a longitudinal direction substantially in a round bar shape and gradually becoming thinner from a first end to a second end in the longitudinal direction, the first end being an end of the measurement site nearest to the subject's shoulder as the arm extends distally outward from the shoulder and the second end being an end of the measurement site farthest from the subject's shoulder, the blood pressure measurement cuff comprising:
a band-shaped body configured to contain an air bladder between an inner cloth that is to come into contact with the measurement site and an outer cloth that opposes the inner cloth, the band-shaped body being configured to be wrapped in a circumferential direction around the measurement site; and
a plate-shaped member provided between the outer cloth and the air bladder in a thickness direction and in a region that corresponds to at least a portion in the circumferential direction of the band-shaped body,
wherein the thickness of the plate-shaped member gradually becomes thinner, with a constant gradient, from the first end to the second end along the longitudinal direction, such that the thickness at the first end is greater than the thickness at a central portion of the plate-shaped member, and the thickness at the central portion is greater than the thickness at the second end.

2. The blood pressure measurement cuff according to claim 1, wherein
a degree to which the thickness of the plate-shaped member gradually becomes thinner from the first end to the second end in the longitudinal direction is set according to a degree to which the measurement site gradually becomes thinner from the first end to the second end in the longitudinal direction.

3. The blood pressure measurement cuff according to claim 1, wherein
the measurement site is a wrist, and
the plate-shaped member is provided to face, when the blood pressure measurement cuff is worn, only a region within a circumference of the wrist and corresponding to a side where a palm of a hand or a back of a hand exists.

4. The blood pressure measurement cuff according to claim 3, wherein
the plate-shaped member curves with a curvature radius that conforms to an outer circumferential surface of the wrist.

5. The blood pressure measurement cuff according to claim 1, wherein
the plate-shaped member is flat in the circumferential direction.

6. The blood pressure measurement cuff according to claim 1, wherein
a length measured in a circumferential direction of the plate-shaped member is constant from the first end to the second end in the longitudinal direction.

7. The blood pressure measurement cuff according to claim 1, wherein
a length measured in a circumferential direction of the plate-shaped member gradually decreases from the first end to the second end in the longitudinal direction.

8. The blood pressure measurement cuff according to claim 1, wherein
the plate-shaped member is composed of a material having elasticity.

9. A blood pressure monitor, comprising:
the blood pressure measurement cuff according to claim 1; and
a main body equipped with an element for blood pressure measurement.

10. The blood pressure monitor according to claim 9, wherein
the plate-shaped member of the cuff includes an element for coupling and integrating the cuff and the main body.

* * * * *